(12) United States Patent
Amit et al.

(10) Patent No.: US 12,247,231 B2
(45) Date of Patent: Mar. 11, 2025

(54) BEE-LESS HONEY

(71) Applicant: TECHNION RESEARCH & DEVELOPMENT FOUNDATION LIMITED, Haifa (IL)

(72) Inventors: Roee Amit, Haifa (IL); Shira Levi, Haifa (IL); Lidya Tannenzapf, Haifa (IL); Yehonatan Zur, Haifa (IL); Ilan Brajzblat, Haifa (IL); Assaf Licht, Haifa (IL); Ofri Warsha, Haifa (IL); Mai Dror, Haifa (IL); Dor Ben Meir, Haifa (IL); Lior Haim, Haifa (IL); Zeinat Awwad, Haifa (IL); Nir Litver, Haifa (IL); Tzila Davidov, Haifa (IL); Liron Abrahami Pachuk, Haifa (IL); Noa Eden, Haifa (IL); Hanriet Tibi, Haifa (IL); Orna Atar, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 636 days.

(21) Appl. No.: 17/503,506

(22) Filed: Oct. 18, 2021

(65) Prior Publication Data

US 2022/0117277 A1 Apr. 21, 2022

Related U.S. Application Data

(60) Provisional application No. 63/093,234, filed on Oct. 18, 2020.

(51) Int. Cl.
| | | |
|---|---|---|
| C12N 1/20 | (2006.01) | |
| A23L 21/25 | (2016.01) | |
| C12N 9/04 | (2006.01) | |
| C12N 9/24 | (2006.01) | |
| C12P 19/02 | (2006.01) | |
| C13K 3/00 | (2006.01) | |

(52) U.S. Cl.
CPC ............ *C12N 9/2402* (2013.01); *A23L 21/27* (2016.08); *C12N 9/0006* (2013.01); *C12P 19/02* (2013.01); *C13K 3/00* (2013.01); *C12Y 101/0301* (2013.01); *C12Y 302/01026* (2013.01)

(58) Field of Classification Search
CPC .......... C12N 9/24; C12N 9/2402; C13K 3/00; A23L 21/27; C12Y 302/01026
See application file for complete search history.

(56) References Cited

PUBLICATIONS

Dubbs JM, Mongkolsuk S. Peroxide-sensing transcriptional regulators in bacteria. J Bacteriol. Oct. 2012;194 (20):5495-503. doi: 10.1128/JB.00304-12. Epub Jul. 13, 2012. PMID: 22797754; PMCID: PMC3458676.
Gem. (2019). Team:Technion-Israel—2019.igem.org. Retrieved Oct. 27, 2022, from https://2019.igem.org/Team:Technion-Israel.

*Primary Examiner* — Tekchand Saidha
(74) *Attorney, Agent, or Firm* — The Roy Gross Law Firm, LLC; Roy Gross

(57) ABSTRACT

Systems comprising a first polynucleotide comprising a regulatory element operatively linked to an open reading frame encoding an invertase enzyme and a second polynucleotide comprising a repressible regulatory element operatively linked to an open reading frame encoding a glucose oxidase enzyme wherein the repressible element inhibits transcription in response to hydrogen peroxide are provided. Cells and compositions comprising a system of the invention, as well as methods using the system of the invention, are also provided, as is artificial honey.

20 Claims, 6 Drawing Sheets
Specification includes a Sequence Listing.

Legend:
S = Supernatant
L = Lysate
E = Elusion

BEE-LESS HONEY

CROSS-REFERENCE TO RELATED APPLICATIONS

This application claims the benefit of priority of U.S. Provisional Patent Application No. 63/093,234 filed Oct. 18, 2020, the contents of which are incorporated herein by reference in their entirety.

FIELD OF INVENTION

The present invention is in the field of bacterial engineering.

BACKGROUND OF THE INVENTION

Honey is a sweet, viscous food substance made by bees. Bees produce honey from floral nectar by regurgitation, enzymatic activity, and water evaporation. The variety of honey produced by honeybees is the best-known, due to its worldwide commercial production and human consumption. Honey gets its sweetness from the monosaccharides fructose and glucose, and has about the same relative sweetness as sucrose (table sugar). It has attractive chemical properties for baking and a distinctive flavor when used as a sweetener. Most microorganisms do not grow in honey, so sealed honey does not spoil, even after thousands of years.

Humans have utilized honey since the dawn of the agricultural revolution for food and traditional medicine. For example, honey was used by ancient Egyptians for medicinal purposes (mentioned 500 times in 900 remedies). In more recent times, honey had been recognized for its antimicrobial activity, which has been attributed to its hydrogen peroxide content and low pH (3.2-4.5).

The chemical composition of honey has been shown to be rather variable. Honey is mainly composed of sugars, of which fructose (31.8-47.4%) and glucose (22.1-40.8%) are the main contributors. Water (16-17%) and sucrose (0.1-3%) are the main other honey components. In addition, hone contains about 200 additional substances in very small concentrations, which include various proteins (e.g. enzymes), peptides, unconjugated amino acids, vitamins, pigments, flavors, aroma substances, and minerals. The concentration of these substances may vary greatly between different honey types. Due to world-wide bee loss, and a desire for a vegan honey alternative, alternative methods of producing honey are greatly desired.

SUMMARY OF THE INVENTION

The present invention provides systems comprising a first polynucleotide comprising a regulatory element operatively linked to an open reading frame encoding an invertase enzyme and a second polynucleotide comprising a repressible regulatory element operatively linked to an open reading frame encoding a glucose oxidase enzyme wherein the repressible element inhibits transcription in response to hydrogen peroxide. Cells and compositions comprising a system of the invention, as well as methods using the system of the invention to produce honey, are also provided.

According to a first aspect, there is provide a system comprising:
i. a first polynucleotide comprising at least one first regulatory element operatively linked to a first open reading frame, wherein the first open reading frame encodes a signal peptide and an invertase enzyme; and
ii. a second polynucleotide comprising a repressible regulatory element operatively linked to a second open reading frame, wherein the second open reading frame encodes a signal peptide and a glucose oxidase enzyme and wherein the repressible regulatory element inhibits transcription of the second open reading frame in response to hydrogen peroxide.

According to another aspect, there is provided a cell comprising the system of the invention.

According to another aspect, there is provided a composition comprising a cell of the invention cultured in a solution comprising sucrose.

According to another aspect, there is provided a composition comprising the cell of the invention cultured in a growth solution devoid of glucose within a semipermeable container, wherein the semipermeable container is configured to allow invertase and glucose oxidase to diffuse out of the growth media and not allow glucose to diffuse into the growth media.

According to another aspect, there is provided a method for producing bee-less honey, the method comprising culturing a cell of the invention in a solution comprising sucrose, thereby producing bee-less honey.

According to another aspect, there is provided an artificial honey solution, comprising at least 40% fructose, at least 30% glucose, at most 10% sucrose and at most 20% water.

According to some embodiments, the invertase is functional to convert sucrose to glucose and fructose.

According to some embodiments, the glucose oxidase is functional to convert glucose to glucono-1,5-lactone and hydrogen peroxide.

According to some embodiments, the first polynucleotide, the second polynucleotide or both is an expression vector.

According to some embodiments, the first regulatory element, the repressible regulatory element or both is a promoter.

According to some embodiments, the promoter is a bacterial promoter.

According to some embodiments, the first regulatory element is a constitutive promoter.

According to some embodiments, the repressible regulatory element comprises a repressible promoter operatively linked to the second reading frame.

According to some embodiments, the repressible element inhibits transcription of the second open reading frame at high hydrogen peroxide levels.

According to some embodiments, the repressible element inhibits transcription of the second open reading frame and the transcriptional inhibition is proportional to hydrogen peroxide levels.

According to some embodiments, the system further comprises a hydrogen peroxide sensitive regulatory element operatively linked to a third reading frame, wherein the third open reading frame encodes a repressor of the repressible regulatory element.

According to some embodiments, the hydrogen peroxide sensitive regulatory element induces transcription of the third reading frame in response to hydrogen peroxide.

In some embodiments, the transcriptional induction is proportional to hydrogen peroxide levels.

According to some embodiments, the hydrogen peroxide sensitive regulatory element and the third reading frame are comprised in a third polynucleotide molecule or are comprises in the second polynucleotide molecule.

According to some embodiments, the hydrogen peroxide sensitive regulatory element is a Pkat promoter, the repressor is LacI, the repressible regulatory element is a Plac promoter, or a combination thereof.

According to some embodiments, the signal peptide is operatively linked to the enzyme to induce secretion of the enzyme by a cell.

According to some embodiments, the system further comprises a fourth polynucleotide molecule comprising a regulatory element operatively linked to a fourth open reading frame, wherein the further open reading frame encodes a catalase enzyme.

According to some embodiments, the catalase is functional to convert hydrogen peroxide to water and oxygen.

According to some embodiments, the cell is a bacterial cell.

According to some embodiments, the bacteria is *B. subtilis*.

According to some embodiments, the cell comprises endogenous expression of a catalase enzyme, and a system of the invention.

According to some embodiments, the polynucleotides are expression vectors functional within the cell.

According to some embodiments, the signal peptides are functional within the cells to induce secretion of proteins to which the signal peptides are operatively linked.

According to some embodiments, the solution comprises between 20-50% sucrose.

According to some embodiments, the cell and growth media for the cell devoid of sucrose are within a semipermeable container and the container is within the solution comprising sucrose and wherein the container is configured to allow invertase and glucose oxidase to diffuse out of the growth media but does not allow glucose to diffuse into the growth media.

According to some embodiments, the cell and growth media for the cell devoid of sucrose are within a semipermeable container and the semipermeable container is within the solution comprising sucrose and wherein the semipermeable container is configured to allow invertase and glucose oxidase to diffuse out of the growth media into the solution comprising sucrose and not allow glucose to diffuse from the media comprising glucose into the growth media.

According to some embodiments, the solution comprises between 20-50% sucrose.

According to some embodiments, the method comprises culturing a composition of the invention within the solution comprising sucrose.

According to some embodiments, the method further comprises adding sucrose to the solution if sucrose concentration in the solution is below a predetermined threshold.

According to some embodiments, the solution is produced by a method of the invention.

According to some embodiments, the solution is devoid of a bee protein, metabolite or byproduct.

According to some embodiments, the solution comprises a bacterial protein selected from invertase and glucose oxidase.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 3B shows a linear scale, while FIG. 3C shows a logarithmic one.

DETAILED DESCRIPTION OF THE INVENTION

Figure 1A:
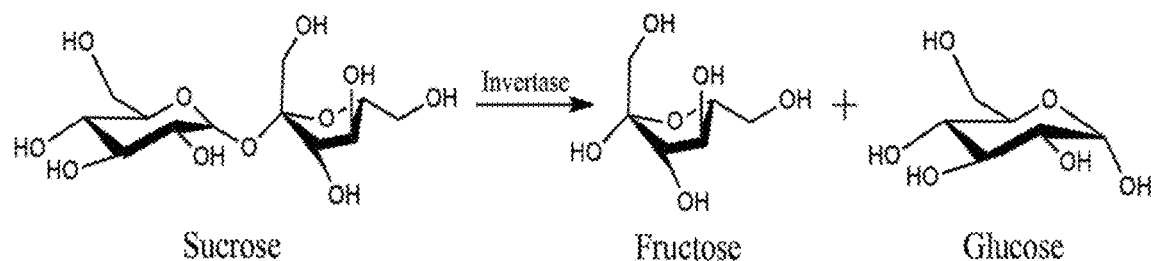
FIGS. 1A-C: Illustrations of various enzymatic reaction of the honey making process. (1A) Illustration of the invertase enzymatic reaction. (1B) Illustration of the glucose oxidase enzymatic reaction. (1C) Illustration of the catalase enzymatic reaction.

The present invention, in some embodiments, provides systems comprising a first polynucleotide comprising a regulatory element operatively linked to an open reading frame encoding an invertase enzyme and a second polynucleotide comprising a repressible regulatory element operatively linked to an open reading frame encoding a glucose oxidase enzyme wherein the repressible element inhibits transcription in response to hydrogen peroxide are provided. Cells and compositions comprising a system of the invention, as well as methods using the system of the invention, are also provided.

By a first aspect, there is provided a system comprising a first polynucleotide comprising a first open reading frame encoding an invertase enzyme and a second polynucleotide comprising a second open reading frame encoding a glucose oxidase enzyme.

In some embodiments, a polynucleotide is a polynucleotide molecule. In some embodiments, the polynucleotide molecule is a nucleic acid molecule. In some embodiments, the polynucleotide is a DNA. In some embodiments, the polynucleotide is an RNA. In some embodiments, the polynucleotide is a plasmid. In some embodiments, the polynucleotide is a vector. In some embodiments, the vector is an expression vector. In some embodiments, the polynucleotide is a viral vector. In some embodiments, the polynucleotide is configured for expression of the open reading frame in a cell. In some embodiments, the cell is a target cell.

The term "expression" as used herein refers to the biosynthesis of a gene product, including the transcription and/or translation of said gene product. Thus, expression of a nucleic acid molecule may refer to transcription of the nucleic acid fragment (e.g., transcription resulting in mRNA or other functional RNA) and/or translation of RNA into a precursor or mature protein (polypeptide). In some embodiments, expression comprises transcription. In some embodiments, expression comprises translation. In some embodiments, expression comprises transcription and translation.

Expressing of a gene, or open reading frame, within a cell is well known to one skilled in the art. It can be carried out by, among many methods, transfection, viral infection, or direct alteration of the cell's genome. In some embodiments, the open reading frame is in an expression vector, plasmid or viral vector.

A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

In some embodiments, the open reading frame is operatively linked to a regulatory element. In some embodiments, the open reading frame is operably linked to a promoter. In some embodiments, the regulatory element is a promoter. The term "operably linked" is intended to mean that a nucleotide sequence, i.e. the open reading frame, is linked to the regulatory element or elements in a manner that allows for expression of the nucleotide sequence (e.g. in an in vitro transcription/translation system or in a host cell when the vector is introduced into the host cell).

In some embodiments, the vector is introduced into the cell by standard methods including electroporation (e.g., as described in From et al., Proc. Natl. Acad. Sci. USA 82, 5824 (1985)), Heat shock, infection by viral vectors, high velocity ballistic penetration by small particles with the nucleic acid either within the matrix of small beads or particles, or on the surface (Klein et al., Nature 327. 70-73 (1987)), and/or the like.

The term "promoter" as used herein refers to a group of transcriptional control modules that are clustered around the initiation site for an RNA polymerase i.e., RNA polymerase II. Promoters are composed of discrete functional modules, each consisting of approximately 7-20 bp of DNA, and containing one or more recognition sites for transcriptional activator or repressor proteins.

In some embodiments, nucleic acid sequences are transcribed by RNA polymerase II (RNAP II and Pol II). RNAP II is an enzyme found in eukaryotic cells. It catalyzes the transcription of DNA to synthesize precursors of mRNA and most snRNA and microRNA.

In some embodiments, mammalian expression vectors include, but are not limited to, pcDNA3, pcDNA3.1 (±), pGL3, pZeoSV2(±), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors, which offer advantages such as lateral infection and targeting specificity, are used for in vivo expression. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

In some embodiments, the regulatory element is an enhancer. In some embodiments, the regulatory element is a repressor. In some embodiments, the regulatory element is an insulator. In some embodiments, the regulatory element is a promoter. In some embodiments, the regulatory element is a repressible regulatory element. In some embodiments, the promoter is an inducible promoter. In some embodiments, the promoter is a constitutive promoter. In some embodiments, the regulatory element is configured to express in a target cell. In some embodiments, the cell is a bacterial cell. In some embodiments, the cell is a mammalian cell. In some embodiments, the cell is an insect cell. In some embodiments, the cell is not an insect cell. In some embodiments, the promoter is a bacterial promoter.

In some embodiments, the first open reading frame is operatively linked to a first regulatory element. In some embodiments, the second open reading frame is operatively linked to a second regulatory element. In some embodiments, the second regulatory element is a repressible regulatory element. In some embodiments, the second regulatory element is a repressive element. In some embodiments, the repressible regulatory element is a repressive element. In some embodiments, the repressive element is an inhibitory element. In some embodiments, the repressive element inhibits transcription of the reading frame. In some embodiments, a repressible regulatory element binds hydrogen peroxide. In some embodiments, the second regulatory element promotes transcription of the second reading frame and transcription is inhibited by hydrogen peroxide. In some embodiments, the inhibition is proportional to the concentration of hydrogen peroxide. In some embodiments, hydrogen peroxide concentration is hydrogen peroxide levels. In some embodiments, concentration is the concentration in the cell comprising the polynucleotide. In some embodiments, concentration is the concentration in the cell comprising the system. In some embodiments, the repressible element is activated in response to hydrogen peroxide. In some embodiments, transcription of the second open reading frame is inhibited in response to hydrogen peroxide. In some embodiments, hydrogen peroxide inhibits transcription of the second open reading frame. In some embodiments, hydrogen peroxide represses activity of the second regulatory element.

In some embodiments, hydrogen peroxide comprises hydrogen peroxide levels. In some embodiments, hydrogen peroxide comprises high levels of hydrogen peroxide. In some embodiments, hydrogen peroxide is hydrogen peroxide above a predetermined threshold. In some embodiments, the response to hydrogen peroxide is proportional to level above the threshold. In some embodiments, hydrogen peroxide levels are levels sufficiently high to repress the repressible regulatory element. In some embodiments, hydrogen peroxide levels are levels sufficient to bind the repressible regulatory element. In some embodiments, high hydrogen peroxide levels are levels sufficiently high to repress the repressible regulatory element. In some embodiments, high hydrogen peroxide levels are levels sufficiently high to harm a cell. In some embodiments, high hydrogen peroxide levels are levels sufficiently high to kill a cell. In some embodiments, high hydrogen peroxide levels are levels sufficiently high to active a Pkat promoter. In some embodiments, the repressible element response to hydrogen peroxide. In some embodiments, the repressible element's transcriptional inhibition is proportional to the concentration of hydrogen peroxide. In some embodiments, the repressible element responds to any amount of hydrogen peroxide and its transcriptional inhibition is proportional to the concentration of hydrogen peroxide. In some embodiments, hydrogen peroxide concentration is hydrogen peroxide levels.

In some embodiments, the predetermined threshold is 0 uM hydrogen peroxide. In some embodiments, the predetermined threshold is 0, 1, 2, 3, 4, 5, 6, 7, 8, 9, 10, 15, 20, 25, 30, 35, 40, 45, or 50 uM hydrogen peroxide. Each possibility represents a separate embodiment of the invention. In some embodiments, the predetermined threshold is 1 uM hydrogen peroxide. In some embodiments, the predetermined threshold is 5 uM hydrogen peroxide. In some embodiments, the predetermined threshold is 10 uM hydrogen peroxide. In some embodiments, the predetermined threshold is 50 uM hydrogen peroxide.

In some embodiments, the second regulatory element comprises a first region that promotes transcription of the second open reading frame and a second region that inhibits transcription upon binding of hydrogen peroxide. In some embodiments, the second regulatory element comprises a first region that promotes transcription of the second open reading frame and a second region that inhibits transcription in response to hydrogen peroxide. In some embodiments, the first region is a promoter. In some embodiments, the promoter is a minimal promoter. In some embodiments, the second region is a repressible element. In some embodiments, the second region is a repressor. In some embodiments, the promoter is a repressible promoter. In some embodiments, repressible is repressible by hydrogen peroxide. In some embodiments, the regulatory element is a hydrogen peroxide sensitive regulatory element.

In some embodiments, hydrogen peroxide binds the second regulatory element. In some embodiments, a repressor binds the second regulatory element. In some embodiments, the system further comprises a hydrogen peroxide sensitive regulatory element operatively linked to a third reading frame. In some embodiments, the third reading frame encodes a repressor molecule. In some embodiments, the repressor molecule is a repressor protein. In some embodiments, the repressor molecule binds to the repressible element. In some embodiments, the repressor molecule binds to the repressor regulatory element. In some embodiments, the repressor molecule is a repressor of the repressible regulatory element. In some embodiments, the repressor molecule represses transcription of the second open reading frame. In some embodiments, binding of hydrogen peroxide to the hydrogen peroxide sensitive regulatory element activates the hydrogen peroxide sensitive regulatory element. In some embodiments, binding of hydrogen peroxide to the hydrogen peroxide sensitive regulatory element activates transcription of the third regulatory element. In some embodiments, hydrogen peroxide activates the hydrogen peroxide sensitive regulatory element, inducing transcription of the repressor molecule, and the repressor molecule binds the repressible regulatory element inhibiting transcription of the second open reading frame.

In some embodiments, transcriptional activation is at high hydrogen peroxide levels. In some embodiments, the transcriptional activation is proportional to hydrogen peroxide concentration. In some embodiments, the transcriptional activation is proportional to hydrogen peroxide levels.

In some embodiments, a third polynucleotide comprises the hydrogen peroxide sensitive regulatory element and the third reading frame. In some embodiments, the third and second polynucleotide molecules are the same polynucleotide. In some embodiments, the second and third polynucleotide molecules are different molecules. In some embodiments, the second polynucleotide further comprises the hydrogen peroxide sensitive regulatory element and the third reading frame. In some embodiments, the first and third polynucleotide molecules are the same molecule. In some embodiments, the first and second polynucleotide molecules are the same molecule. In some embodiments, the first and third polynucleotide molecules are different molecules. In some embodiments, the first and second polynucleotide molecules are different molecules. In some embodiments, the first, second and third polynucleotide molecules are the same molecule. In some embodiments, the first, second and third polynucleotide molecules are all different molecules.

Elements that respond to hydrogen peroxide are well known in the art, and any such element may be employed. These elements include, for examples, the *Arabidopsis* Glutathione-S-transferase promoter, the HSP10A promoter, the OxyR element, and the PerR element. Further such elements are also disclosed in Dubbs and Mongkolsuk, 2012, "Peroxide-sensing transcriptional regulators in bacteria", J. Bacteriology, 194(20): 5495-503, and Marinho et al., 2014, "Hydrogen peroxide sensing, signaling and regulation of transcription factors" Redox Biology, 2: 535-562, herein incorporated by reference in their entirety. In some embodiments, the hydrogen peroxide sensitive regulatory element comprises the Pkat promoter. In some embodiments, the hydrogen peroxide sensitive regulatory element consists of the Pkat promoter. In some embodiments, the Pkat promoter comprises the sequence ataactattttataataattataaataatattgactttttacttagagatgatattatgttctta (SEQ ID NO: 1). In some embodiments, the Pkat promoter consists of SEQ ID NO: 1. In some embodiments, the Pkat element comprises or consists of SEQ ID NO: 1.

Repressible elements are well known in the art and any such element may be employed. Examples of repressible elements include, but are not limited to, the Plac element, the Tet repressible element, and Trp element, whose corresponding repressors are Lac, Tet and Trp. In some embodiments, the repressible regulatory element is the Plac element. In some embodiments, the Plac element is the Plac promoter. In some embodiments, the repressor molecule is LacI. In some embodiments, the Plac promoter comprises the sequence ctcgagggtaaatgtgagcactcacaattcattttgcaaaagttgttgactttatcta-caaggtgtggcataatgtgtgtaattgtgagc ggataacaatt (SEQ ID NO: 2). In some embodiments, the Plac promoter consists of SEQ ID NO: 2. In some embodiments, LacI is encoded by the sequence atgaaaccagtaacgttatac-gatgtcgcagagtatgccggtgtctcttatcagaccgtttcccgcgtggt-gaaccaggccagccac gtttctgcgaaaacgcgggaaaaagtggaagcggc-gatggcggagctgaattacattcccaaccgcgtggcacaacaactggc gggcaaacagtcgttgctgattggcgttgc-cacctccagtctggccctgcacgcgccgtcgcaaattgtcgcggcgattaaatctc gcgccgatcaactgggtgccagcgtggtggtgtc-gatggtagaacgaagcggcgtcgaagcctgtaaaacgccggtgcacaat cttctcgcgcaacgcgtcagtgggctgatcattaactatccgctggatgaccag-gatgccattgctgtggaagctgcctgcactaat gttccggcgttatttctt-gatgtctctgaccagacacccatcaacagtattatttttctcccatgaa-gacggtacgcgactgggcgtgga gcatctggtcgcattgggtcaccagcaaatcgcgctgttagcgggcccat-taagttctgtctcggcgcgtctgcgtctggctggctg gcataaatatct-cactcgcaatcaaattcagccgatagcggaacgggaaggcgactggagtgc-catgtccggttttcaacaaacca tgcaaatgctgaatgagggcatcgttcccactgcgatgctggttgccaacgatca-gatggcgctgggcgcaatgcgcgccattac cgagtccgggctgcgcgttggtgcggatatctcggtagtgggatacgacga-taccgaagacagctcatgttatatcccgccgtcaa ccaccatcaaacaggat-tttcgcctgctggggcaaaccagcgtggaccgcttgctgcaactctctcaggg-ccaggcggtgaagg gcaatcagctgttgcccgtctcactggtgaaaagaaaaac-caccctggcgcccaatacgcaaaccgcctctccccgcgcgttggc cgattcat-taatgcagctggcacgacaggtttcccgactggaaagcgggcagtaataa (SEQ ID NO: 3).

In some embodiments, the first open reading frame encodes an invertase enzyme. In some embodiments, an invertase enzyme is invertase. In some embodiments, the invertase enzyme is functional to convert sucrose to glucose and fructose. In some embodiments, the invertase converts a single sucrose molecule into a single glucose molecule and single fructose molecule. In some embodiments, the invertase is *A. niger* invertase. In some embodiments, the *A. niger* invertase is encoded by the sequence atgaagctt-caaacggcttccgtactgctcggcagtgctgcggctgcctctccttcaatgca-gacgcgggcctccgtgatcatcgac tacaatgtcgctcctccaaacctctc-caccctgcccaatggctccctcttcgaaacatggcgtccccgcgcccacgtcct-gccccca aacggcagatcggtgaccectgcctgcattacaccgatcccgc-cacgggcctcttccacgtcggcttccttcacgatggcagcgg catctccagtgc-caccaccgatgacctacccacctaccaagacctcaaccaaggcaaccaagtcat-tgtccccggaggcatcaac gaccccgtcgctgtcttcgacggctcagtcatccccaacggcat-caacggcctccccaccctcctctacacctccgtctcctacctc cccatc-cactggtccatccctacacccgcggcagtgagacc-caatccctcgccgtctcctccgacggcggcagcaacttcacca agctcgaccagggccccgtcatccctggccctccttcgcctacaacgtcaccg-cattccgggaccctacgtcttccaaaacccc acactcgaatccctcctc-cacagcaagaacaacacctggtacaccgt-catctccggtggtctgcacgaaaagggccccgcccaat tcctctaccgtcagtacgactcggacttccagtactgggagtacctcggc-caatggtggcacgaacccaccaactccacctggggt aacggcacctgggccggccgctgggccttcaacttcga-gaccggcaacgtcttcagtctcgacgagtacggatacaaccccac ggcca-gatcttcaccaccatcggcaccgagggctctgacctgcccgtcgtgccccagct-caccagcatccacgacatgctctggg tgtccggtacagtctcccgcaatggctctgtctctttcaccccccaa-catggcgggctcctcgattggggctctcctcttacgctgct gccg-gaaaggttctccccctcgacttctctgccttccacgaagagcggcgccccg-gaacgcttcatctcgtacgtctggctgtccggt gacctgttcgaacaggccgaaggattccccacgaaccagcagaat-tggaccggtacgctgctgcttccgcgtgagttgcgcgtgc tgtatatccc-caatgtggtggacaatgtctggcccgggagtctggtgcctcgtggcaggtcgt-gagcagcgacagcagtgcggg caccgtcgagctgcagacgctgggtatctccattgcccgggaaac-caaggccgcgttgctgtcgggaacgtcgttcactgagtcc ggccgcacct-gaacagcagcggtgttgttccgttcaagcgctcgc-catccgagaagttcttcgttctgtccgcacagctgtccttc cctgcgtcggctagaggatcgggacttaagagtggattccagatcctctcatcg-gagcacgaaagtaccaccgtgtactaccaatt ctcgaatgagtcgattatcgtc-gatcgcagcaacactagtgctgcggcgcgcacgactgatggcatcga-tagcagtgcagaagct ggcaagttgcgtctatttgactgtgctgaatggcggagagcaggccattga-gacgctagatttgactctcgtggtggataactccgtg ttggagatgtatgc-caatggtcggtttgcgttgagtacttgggttcgg (SEQ ID NO: 4). In some embodiments, the invertase consists of SEQ ID NO: 4. In some embodiments, the invertase comprises SEQ ID NO: 4. In some embodiments, the invertase coding sequence has been optimized for expression in a target cell. In some embodiments, optimized is codon optimized. In some embodiments, the target cell is a bacterium. In some embodiments, the bacterium is *B. subtilis*. In some embodiments, invertase codon optimized for expression in *B. subtilis* comprises the sequence atgaagctt-caaacggcttcagtactgctcggcagcgctgcggctgcctctccttcaatgca-gacgcgggcctcagtgatcatcga ctacaatgtcgctcctccaaacctct-caaccctgccgaatggctcactcttcgaaacatggcgtccgcgcgcccacg-tcctgccgc caacggcagatcagtgaccectgcctgcattacaccgatcccgc-cacgggcctcttccacgtcggcttccttcacgatggcagc ggcatctcaagcgc-caccaccgatgacctgccgacctaccaagacctcaaccaaggcaaccaagtcat-tgtcccgggaggcatc aacgacccggtcgctgtcttcgacggctcagtcatcccgaacggcat-caacggcctcccgacctcctctacacctcagtctcata cctcccgatccactggt-caatcccgtacaccegcggcagcgagacccaatcactcgccgtctcatca-gacggcggcagcaacttc accaagctcgaccagggcccggtcatccctggccctccgttcgcctacaacgtcaccgcattccgggacccgtacgtcttccaaa acccgacactcgaatcactcctcacagcaagaacaacacctggtacaccgt-catctcaggtggtctgcacgaaaagggcccgg cccaattcctctaccgtcagtacgactcagacttccagtactgggagtacctcggc-caatggtggcacgaaccgaccaactcaacc tggggtaacggcacctgggccggacgctgggccttcaacttcga-gaccggcaacgtcttcagcctcgacgagtacggatacaac ccgcacggcca-gatcttcaccaccatcggcaccgagggctctgacctgccggtcgtgccgcagct-caccagcatccacgacatg ctctgggtgtcaggtacagtctcacgcaatggctctgtctctttcaccccgaa-catggcgggcetcctcgattggggcttctcatctta cgctgctgccg-gaaaggttctcccgtcaacttctctgccttcaacgaagagcggcgcccg-gaacgcttcatctcatacgtctggct gtcaggtgacctgttcgaacaggccgaaggattcccgacgaaccagcagaat-tggaccggtacgctgctgcttccgcgtgagttg cgcgtgctgtatatcccgaatgtggtggacaatgctctggcccgg-gagtctggtgcctcatggcaggtcgtgagcagcgacagca gcgcgggcaccgtcgagcttcagacgctgggtatctcaattgcccgggaaac-caaggccgcgttgctgtcaggaacgtcattcac tgagtcaggacgcaccct-gaacagcagcggtgttgttccgttcaagcgctcac-catcagagaagttcttcgttctgtcagcacagct gtcattccctgcgtcagctagaggatcaggacttaagagcggattccagatcctct-catcagagcacgaaagcaccaccgtgtact accaattctcaaatgagtcaat-tatcgtcgatcgcagcaacactagcgctgccggcgcgcacgactgatggcatcga-tagcacgcgc agaagctggcaagttgcgtctgtttgacgtgctgaatggcggagagcaggccatt-gagacgctggatttgactctcgtggtggata actcagtgttggagatgtatgc-caatggtcggtttgcgttgagcacttgggttcgg (SEQ ID NO: 5). In some embodiments, the invertase consists of SEQ ID NO: 5. In some embodiments, the invertase comprises SEQ ID NO: 5.

In some embodiments, the second open reading frame encodes a glucose oxidase enzyme. In some embodiments, a glucose oxidase enzyme is glucose oxidase. In some embodiments, the glucose oxidase is functional to convert glucose to glucono-1,5-lactone and hydrogen peroxide. In some embodiments, the invertase converts a single glucose molecule into a single glucono-1,5-lactone molecule and single hydrogen peroxide molecule. In some embodiments, the invertase converts a single glucose molecule and a single oxygen molecule into a single glucono-1,5-lactone molecule and single hydrogen peroxide molecule. In some embodiments, the glucose oxidase is *A. niger* glucose oxidase.

In some embodiments, the *A. niger* glucose oxidase is encoded by the sequence atgcagactctccttgt-gagctcgcttgtggtctccctcgctgcggccctcccacactacatcag-gagcaatggcatcgaagccag cctcctgactgaccc-caaggaggttgccggccgcactgtcgactacatcatcgctggtggaggtct-gactggactcaccactgctg cccgtctgacggagaaccccgatat-cactgtgcttgtcatcgaaagtggctcctacgagtctgacagaggtcctatcatt-gaggacc tgaacgcttacggtgacattttggcagcagtgtggaccacgcc-tacgagactgtcgagctcgccaccaacaatcagactgcgctg atccgctccgaaatggtctcggtggctctaccctcgt-caacggtggcacctggactcgccccacaaggcacaagttgactcatg gga-gaccgtcttcggaaatgagggctggaactgggacagcgtggccgcc-tactccctccaggctgagcgtgctcgcgcaccaa atgccaaacagattgctgctggccactactttaatgcatcctgccatggtat-caatggtactgtccacgccggaccccgcgataccg gtgatgactactccc-catcgtcaaggctctcatgagcgctgtcgaagacaggggcgttcccac-caagaaggacttgggatgcgg tgaccccatggtgtgtccatgttcccaacaccttgcacgaagac-caagtgcgctctgatgccgctcgcgaatggctcctcccca actaccagcgtcc-caacctgcaagtcctcactggacagtatgttg-gaaaggtcctgctcagccagaacgctaccacacctcgtgcc gttggcgtggaattcggcacccacaagggcaacacccacaacgtc-tacgctaagcacgaggtcctcctggccgctggatccgct gtctccac-
catcctcgaatattccggtatcggaatgaagtccattctagagcctcttggaat-tgacaccgtcgttgacctgcccgt tggtctcaaccttcaggaccagaccacctctaccgtccgctcacgcat-tacctccgccggtgccggacagggacaggccgcttgg ttcgctaccttcaacga-gacctttggcgactacgccgaaaaggctcacgagctgctcaacaccaagctg-gagcagtgggccgaa gaggccgtcgcccgtggccggattccacaacaccaccgcctttgct-catccagtacgagaactaccgcgactggatcgtcaaggac aatgtcgcat-actcggaactcttcctcgacacggccggagtggccagtttcgatgtgtgg-gatcttctgcccttcactagaggatacg tacacatcctcgacaaggaccccacctccgccatttcgcat-acgaccctcagtactttctcaacgagcttgacctgctcggccagg ctgccgc-cactcagctggcccgcaacatctccaactccggtgccatgcaaacttatttcgctg-gagagactattcccggtgacaac ctcgcgtatgatgccgacttgagcgcctgggttgagtatatcccgta-caacttccgccctaactaccatggtgtgggtacttgctccat gatgccgaaggagatgggccggtgttgtcgacaatgctgcccgtgtgtatg-gtgtgcagggactgcgagtcatcgatggttctatcc ccctacgcaaatgtcgtcc-catgttatgacggtctttatgccatggccttgaagattgcggatgccatcttggcg-gattatgcttccat gcag (SEQ ID NO: 6). In some embodiments, the glucose oxidase consists of SEQ ID NO: 6. In some embodiments, the glucose oxidase comprises SEQ ID NO: 6. In some embodiments, the glucose oxidase coding sequence has been optimized for expression in a target cell. In some embodiments, glucose oxidase codon optimized for expression in *B. subtilis* comprises the sequence atgcagactctccttgttagctcacttgtggtctccctcgctgcggccctgccacacta-catcagaagcaatggcattgaagccagc ctcctgact-gatccgaaggatgtctccggacgcacggtcgactacatcatcgctggtgga-ggtctgactggactcaccaccgctgc tcgtctgacggagaacccgaa-catcagtgtgctcgtcatcgaaagtggctcctacgagtcagacagaggtcctat-cattgaggacc tgaacgcctacggcgacatctttggcagcagtgtagac-cacgcctacgagaccgtggagctggctaccaacaatcaaaccgcgc tgatccgctccgaaatggtctcggtggctctactctggt-gaatggtggcacctggactcgccccgcacaaggcacaggttgactctt ggga-gactgtctttggaaatgagggctggaactgggacaatgtggccgcc-tactccctccaggctgagcgtgctcgcgcaccaa atgccaaacagatcgctgctggccactacttcaacgcatcctgccatggtgt-taatggtactgtccatgccggaccgcgcgacacc ggcgatgactattctcc-gatcgtcaaggctctcatgagcgctgtcgaagaccggggcgttccgac-caagaaagacttcggatgcg gtgacccgcatggtgtgtccatgttcccgaacaccttgcacgaagac-caagtgcgctccgatgccgctcgcgaatggctgcttccg aactac-caacgtccgaacctgcaagtcctgaccggacagtatgttggtaaggtgctcct-tagccagaacgccacccccgcgtg ccgttggcgtggaatttggcacccacaaagggcaacacccacaacgtt-tacgctaagcacgaggtcctcctggccgcgggctccg ctgtctctccgacaatcctcgaatattccggtatcggaatgaagtccatcctg-gagccgcttggtatcgacaccgtcgttgacctgcc ggtcggcttgaacctgcaa-gaccagaccaccgctaccgtccgctcccgcat-cacctctgctggtcaggacagggacaggccg cttggttcgccaccttcaacgagacctttggtgactat-tccgaaaaggcacacgagctgctcaacaccaagctggagcagtgggcc gaagaggccgtcgcccgtggcggattccacaacaccaccgccttgct-catccagtacgagaactaccgcgactggattgtcaacc acaacgtcgcgtactcagaactcttcctcgacactgccggagtagccagcttc-gatgtgtgggaccttctgccgttcacccgtggat acgttca-catcctcgacaaggacccgtaccttcaccacttcgcctacgaccctcagtacttcct-caacgagctggacctgctcggtc
aggctgccgctactcaactggcccgcaacatctccaactccggtgccatgca-gacctacttcgctggggagactatcccgggtgat aacctcgcgtatgatgccgat-tgagcgcctggactgagtacatcccgtaccacttccgtcctaactac-catggcgtgggtacttgct ccatgatgccgaaggagatgggcggtgttgttga-taatgctgcccgtgtgtatggtgtgcagggactgcgtgtcattgatggttctat tcctcctacgcaaatgtcatcccatgtcatgacggtgttctatgccatggcgct-gaaaatttcagatgctatcttggaagattatgcttcc atgcag (SEQ ID NO:

7). In some embodiments, the invertase consists of SEQ ID NO: 7. In some embodiments, the invertase comprises SEQ ID NO: 7.

In some embodiments, the open reading frame further comprises a signal peptide. In some embodiments, the open reading frame further encodes a signal peptide. In some embodiments, the signal peptide is a leader peptide. Signal peptides and leader peptides are well known in the art and allow for secretion of the protein comprising the peptide. In some embodiments, the signal peptide is operatively linked to the protein encoded by the open reading frame. In some embodiments, the signal peptide is operatively linked to the enzyme. In some embodiments, the signal peptide is N-terminal. In some embodiments, the signal peptide induces secretion of the enzyme by a cell. In some embodiments, operatively linked comprises an open reading frame encoding a single protein comprising the signal peptide and the enzyme. In some embodiments, the first open reading frame comprises/encodes a signal peptide. In some embodiments, the second open reading frame comprises/encodes a signal peptide. In some embodiments, the third open reading frame does not comprise/encode a signal peptide. In some embodiments, the invertase protein comprises a signal peptide. In some embodiments, the glucose oxidase comprises a signal peptide. In some embodiments, the repressor protein does not comprise a signal peptide. In some embodiments, the repressor protein is devoid of a signal peptide. In some embodiments, the signal peptide is configured for secretion from a target cell. In some embodiments, the signal peptide is the AmyE signal peptide. In some embodiments, the AmyE signal peptide comprises MFAKRFKTSLLPLF-AGFLLLFHLVLAG (SEQ ID NO: 8). In some embodiments, the AmyE signal peptide consists of SEQ ID NO: 8. In some embodiments, the AmyE signal peptide comprises MFAKRFKTSLLPLFAGFLLLFHLVLAGPAAASA (SEQ ID NO: 9). In some embodiments, the AmyE signal peptide consists of SEQ ID NO: 9. In some embodiments, the AmyE signal peptide is encoded by a sequence comprising atgtttgcaaaacgattcaaaacctctttactgccgttattcgctggatttttat-tgctgtttcatttggttctggcagga (SEQ ID NO: 10). In some embodiments, the AmyE signal peptide is encoded by a sequence consisting of SEQ ID NO: 10. In some embodiments, the AmyE signal peptide is encoded by SEQ ID NO: 10. In some embodiments, the AmyE signal peptide is encoded by a sequence comprising atgtttgcaaaacgatt-caaaacctctttactgccgttattcgctggattttttattgctgtttcat-ttggttctggcaggaccggcggctgc gagtgct (SEQ ID NO: 11). In some embodiments, the AmyE signal peptide is encoded by a sequence consisting of SEQ ID NO: 11. In some embodiments, the AmyE signal peptide is encoded by SEQ ID NO: 11. Any signal peptide effective to induce secretion in the target cell may be employed. In some embodiments, the ATG start codon is provided in the signal peptide and the protein attached to the signal peptide lacks the start codon. In some embodiments, any one of SEQ ID NO: 3-7 lacks the ATG start codon. In some embodiments, SEQ ID NO: 3 lacks the start codon. In some embodiments, SEQ ID NO: 4 lacks the start codon. In some embodiments, SEQ ID NO: 5 lacks the start codon. In some embodiments, SEQ ID NO: 6 lacks the start codon. In some embodiments, SEQ ID NO: 7 lacks the start codon.

In some embodiments, the system further comprises a fourth polynucleotide. In some embodiments, the fourth polynucleotide molecule comprises an open reading frame encoding a catalase enzyme. In some embodiments, the fourth open reading frame is operatively linked to a fourth regulatory element. In some embodiments, the fourth regulatory element is a constitutive promoter. In some embodiments, the catalase enzyme is catalase. In some embodiments, the catalase enzyme is functional to convert hydrogen peroxide to water and oxygen. In some embodiments, the fourth polynucleotide molecule is different than any of the first, second and third molecules. In some embodiments, the fourth molecule is that same as any of the first, second, third molecule or a combination thereof.

In some embodiments, an open reading frame further encodes a tag. In some embodiments, the tag is a protein tag. In some embodiments, the tag is in frame with the other protein encoded by the open reading frame. In some embodiments, the tag is a C-terminal tag. In some embodiments, the tag is an N-terminal tag. In some embodiments, the tag is internal to the protein. In some embodiments, the tag is a detectable tag. In some embodiments, the tag is a purification tag. In some embodiments, the tag is cleavable. In some embodiments, the cleavable protein sequence is encoded between the tag and the protein encoded by the open reading frame. Tags are well known in the art and any tag may be used. In some embodiments, the tag is a His tag. In some embodiments, the tag is a 6× His tag.

In some embodiments, the open reading frame further encodes a linker. In some embodiments, the linker is between the signal peptide and the protein encoded by the open reading frame. In some embodiments, the linker is between the protein encoded by the open reading frame and the tag. In some embodiments, the protein encoded by the open reading frame is invertase. In some embodiments, the protein encoded by the open reading frame is glucose oxidase. In some embodiments, the protein encoded by the open reading frame is glucose catalase. In some embodiments, linker is a peptide linker. In some embodiments, the linker is a flexible linker. In some embodiments, the linker comprises at least 1 amino acid. In some embodiments, the linker comprises at least 1, 2, 3, 4, 5, 6, 7, 8 or 9 amino acids. Each possibility represents a separate embodiment of the invention. In some embodiments, the linker comprises RPVHIWSSV (SEQ ID NO: 12). In some embodiments, the linker consists of SEQ ID NO: 12. In some embodiments, the linker is encoded by a nucleic acid sequence comprising cggccggtgcacatatggagctcggta (SEQ ID NO: 13). In some embodiments, the linker is encoded by a nucleic acid sequence consisting of SEQ ID NO: 13. In some embodiments, the linker is encoded by SEQ ID NO: 13.

By another aspect, there is provided a polynucleotide molecule comprising an open reading frame comprises SEQ ID NO: 5.

By another aspect, there is provided a polynucleotide molecule comprising an open reading frame comprises SEQ ID NO: 7.

By another aspect, there is provided a cell comprising a system of the invention.

By another aspect, there is provided a cell comprising a polynucleotide of the invention.

In some embodiments, the cell is a bacterial cell. In some embodiments, the cell is a *B. subtilis* cell. In some embodiments, the cell is an excretory cell. In some embodiments, the cell is a prokaryotic cell. In some embodiments, the cell is a eukaryotic cell. In some embodiments, the cell is suitable for human consumption. In some embodiments, the cell comprises endogenous expression of a catalase enzyme. In some embodiments, the cell endogenously expresses a catalase enzyme. In some embodiments, the expression vectors are functional within the cell. In some embodiments, the function comprises transcription. In some embodiments, the signal peptide is functional in the cell to induce secretion of the proteins to which the signal peptides are operatively linked. In some embodiments, the signal peptide is functional induce secretion from the cell.

In some embodiments, the cell is a population of cells. In some embodiments, the cell is enclosed in a membrane. In some embodiments, the membrane is a permeable membrane. In some embodiments, the membrane is a semipermeable membrane. In some embodiments, the membrane is functional to allow secreted enzymes to exit. In some embodiments, the membrane is functional to allow hydrogen peroxide to enter. In some embodiments, the membrane does not allow the cells to exit. In some embodiments, the membrane allows sugars to enter. In some embodiments, the membrane does not allow sugars to enter.

By another aspect, there is provided a composition comprising a cell of the invention and a solution comprising sucrose.

By another aspect, there is provided a composition comprising a cell of the invention and growth media within a membrane.

In some embodiments, the cell is cultured in the solution. In some embodiments, the solution is media. In some embodiments, the solution is culture media. In some embodiments, the culture media is culture media for the cell. In some embodiments, the media is growth media. In some embodiments, the media is chemically defined media. In some embodiments, the solution comprising sucrose is not growth media. In some embodiments, the solution comprising sucrose does not comprise growth factors. In some embodiments, the solution comprising sucrose is sugar water. In some embodiments, the solution comprising sucrose is devoid of proteins.

As used herein, the term "chemically defined media" refers to a medium in which all the chemical components are known. In some embodiments, chemically defined media is devoid of animal-based products. In some embodiments, chemically defined media is devoid of animal-based proteins. In some embodiments, the media is protein free media.

In some embodiments, the membrane encloses the cell and growth media. In some embodiments, growth media is culture media. In some embodiments, growth media comprises growth factors. In some embodiments, the media inside the membrane is devoid of sucrose. In some embodiments, the media outside the membrane comprises sucrose. In some embodiments, the growth media is chemically defined media.

In some embodiments, the membrane is a semipermeable membrane. In some embodiments, the membrane is a container. In some embodiments, the membrane is a semipermeable container. In some embodiments, the membrane is not permeable to sucrose.

In some embodiments, the membrane does not allow sucrose diffusion into the growth media. In some embodiments, the membrane does not allow sucrose diffusion into the container. In some embodiments, the membrane is configured not to allow sucrose diffusion into the container. In some embodiments, growth media inside the membrane is growth media for the cell. In some embodiments, the solution outside the membrane is chemically defined media. In some embodiments, the membrane is not permeable to the growth factors in the media. In some embodiments, the membrane is configured to allow invertase and glucose oxidase to diffuse out of the membrane. In some embodiments, the membrane is permeable to proteins. In some embodiments, the growth media is chemically defined media, and the solution is chemically defined media comprising sucrose and the membrane is impermeable to sucrose and permeable to proteins.

In some embodiments, the solution comprises at least 10% sucrose. In some embodiments, the solution comprises at least 20% sucrose. In some embodiments, the solution comprises at least 5, 10, 20, 25, 30, 40, 50, 60, 70, 75, 80, 90, 95, 97 or 100% sucrose. Each possibility represents a separate embodiment of the invention. In some embodiments, the solution comprises between 10-90, 10-75, 10-50, 10-40, 10-30, 10-25, 10-20, 15-90, 15-75, 15-50, 15-40, 15-30, 15-25, 15-20, 20-90, 20-75, 20-50, 20-40, 20-30, 20-25, 25-90, 25-75, 25-50, 25-40, 25-30, 30-90, 30-75, 30-50, 30-40, 40-90, 40-75, or 40-50% sucrose. Each possibility represents a separate embodiment of the invention. In some embodiments, the solution comprises between 20-50% sucrose. In some embodiments, the solution comprises between 10-50% sucrose. In some embodiments, the solution comprises between 20-40% sucrose. In some embodiments, the solution is an aqueous solution. In some embodiments, the solution comprises at least 10% water. In some embodiments, the solution comprises at least 20% water. In some embodiments, the solution comprises at least 25% water. In some embodiments, the solution comprises at least 30% water.

By another aspect, there is provided a method for producing honey, the method comprising culturing a cell of the invention is a solution comprising sucrose, thereby producing honey.

In some embodiments, the honey is an artificial honey. In some embodiments, the honey is bee-less honey. In some embodiments, honey is a honey like solution. In some embodiments, the honey comprises a moisture percentage of less than 20%. In some embodiments, the honey comprises a moisture percentage of less than 20, 22, 24, 25, 26, 28, 30, 35, 40, 45 or 50%. Each possibility represents a separate embodiment of the invention.

In some embodiments, the moisture percentage is the percentage of water. In some embodiments, the honey comprises at most 20% water. In some embodiments, the honey comprises an acidic pH. In some embodiments, the honey comprises a pH less than 5. In some embodiments, the honey comprises a pH less than 4.

In some embodiments, the honey is a combination of sucrose, fructose and glucose. In some embodiments, the honey is devoid of sugars other than sucrose, fructose and glucose. In some embodiments, the honey is a combination of fructose and glucose. In some embodiments, sucrose, fructose and glucose are in a ratio that is similar to natural honey. In some embodiments, fructose and glucose are in a ratio that is similar to natural honey. In some embodiments, similar is within plus/minus 10%. In some embodiments, similar is within plus/minus 5%. In some embodiments, similar is within plus/minus 20%. In some embodiments, the honey is substantially devoid of sucrose. In some embodiments, the honey is substantially depleted of sucrose. In some embodiments, the honey comprises fructose. In some embodiments, the honey comprises more molecules of fructose than glucose. In some embodiments, the honey comprises a larger percentage of fructose than glucose. In some embodiments, the honey comprises equal amount of fructose and glucose. In some embodiments, the honey comprises a ratio of fructose to glucose of about 60:40. In some embodiments, the honey comprises a ratio of fructose to glucose of at least 1:1. In some embodiments, the honey comprises a ratio of fructose to glucose 1.1:1. In some embodiments, the honey comprises a ratio of fructose to glucose 1.2:1. In some embodiments, the honey comprises a ratio of fructose to glucose 1.3:1. In some embodiments, the honey comprises a ratio of fructose to glucose 1.4:1. In some embodiments, the honey comprises a ratio of fructose to glucose 1.5:1. In some embodiments, the honey comprises at least 30% glucose. In some embodiments, the honey comprises at least 25% glucose. In some embodiments, the honey comprises at least 35% glucose. In some embodiments, the honey comprises about 35% glucose. In some embodiments, the honey comprises between 20-50% glucose. In some embodiments, the honey comprises between 20-40% glucose. In some embodiments, the honey comprises between 30-50% glucose. In some embodiments, the honey comprises between 30-40% glucose. In some embodiments, the honey comprises at least 50% fructose. In some embodiments, the honey comprises at least 45% fructose. In some embodiments, the honey comprises at least 40% fructose. In some embodiments, the honey comprises at least 30% fructose. In some embodiments, the honey comprises at least 35% fructose. In some embodiments, the honey comprises about 50% fructose. In some embodiments, the honey comprises between 20-50% fructose. In some embodiments, the honey comprises between 20-40% fructose. In some embodiments, the honey comprises between 30-50% fructose. In some embodiments, the honey comprises between 30-40% fructose. In some embodiments, the honey comprises between 40-50% fructose. In some embodiments, the honey comprises between 45-50% fructose. In some embodiments, the honey comprises at most 10% sucrose. In some embodiments, the honey is devoid of sucrose. In some embodiments, the honey comprises at most 20, 19, 18, 17, 16, 15, 14, 13, 12, 11, 10, 9, 8, 7, 6, 5, 4, 3, 2, or 1% sucrose. Each possibility represents a separate embodiment of the invention. In some embodiments, the honey comprises at most 10% sucrose. In some embodiments, the honey comprises a ratio of fructose to glucose of at least 1:1 and a ratio of fructose to glucose to sucrose of at least 1:1:0.25. In some embodiments, the honey comprises at most 30, 227, 25, 22, 20, 17, 15, 12, 10, 7 or 5% water. Each possibility represents a separate embodiment of the invention. In some embodiments, the honey comprises at most 20% water. In some embodiments, the honey comprises at least 40% fructose, at least 30% glucose, at most 10% sucrose and at most 20% water.

In some embodiments, the method comprises culturing a composition of the invention in a solution comprising sucrose. In some embodiments, culturing is incubating. In some embodiments, culturing is for a time sufficient to produce the honey. In some embodiments, culturing is under conditions sufficient to produce the honey. In some embodiments, the time is at least a time sufficient to produce the honey. In some embodiments, the time is a time sufficient to substantially deplete the solution of sucrose. In some embodiments, the time is a time sufficient to use up all the sucrose. In some embodiments, the time is a time sufficient to produce a solution substantially devoid or substantially depleted of sucrose. It will be understood by a skilled artisan that due to the system of the invention the solution will reach a steady state where there is equilibrium between the glucose and fructose. In some embodiments, the time is a time sufficient to produce a solution in equilibrium between glucose and fructose.

In some embodiments, the method comprises adding additional sucrose to the solution. In some embodiments, sucrose is added when the sucrose concentration in the solution is at or below a predetermined threshold. In some embodiments, sucrose is added is the sucrose concentration in the solution is at or below a predetermined threshold. In some embodiments, the predetermined threshold is a concentration of zero. In some embodiments, the threshold is a concentration of 1, 2, 3, 4, 5, 10, 15, 20 or 25% sucrose. Each possibility represents a separate embodiment of the invention. In some embodiments, the threshold is a concentration of 5% sucrose. In some embodiments, the threshold is a concentration of 10% sucrose.

In some embodiments, the method further comprises removing water from the solution. In some embodiments, the removing is after the culturing. In some embodiments, removing is evaporating. In some embodiments, removing is dehydrating. In some embodiments, the removing is performed until the solution comprises a water content that is equivalent to water. In some embodiments, the removing is performed until the solution comprises a water content below 20%. In some embodiments, the removing is performed until the solution comprises a water content below 30, 25, 22, 20, 17, 15, 12, 10 or 5%. Each possibility represents a separate embodiment of the invention.

By another aspect, there is provided artificial honey.

In some embodiments, the artificial honey is an artificial honey composition. In some embodiments, the artificial honey is an artificial honey solution. In some embodiments, the artificial honey is produced by a method of the invention. In some embodiments, the artificial honey is bee-free honey. In some embodiments, the artificial honey is honey not found in nature. In some embodiments, the honey is devoid of a bee protein. In some embodiments, a bee is a Apis. In some embodiments, a bee is a member of the clade Anthophilia. In some embodiments, the bee is a honeybee. In some embodiments, the honey is devoid of an Apis protein. In some embodiments, the honey is devoid of an Anthophila protein. In some embodiments, the honey is devoid of a bee byproduct. In some embodiments, the honey is devoid of a bee metabolite. In some embodiments, the honey comprises a bacterial protein. In some embodiments, the protein is invertase. In some embodiments, the protein is glucose oxidase. In some embodiments, the protein is a protein not naturally secreted by bacteria. In some embodiments, the bacterial is *B. subtilis*. In some embodiments, the bacteria is *A. niger*. In some embodiments, the honey comprises a bacterial byproduct. In some embodiments, the honey comprises a bacterial metabolite.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Example 1

Figure 1B:
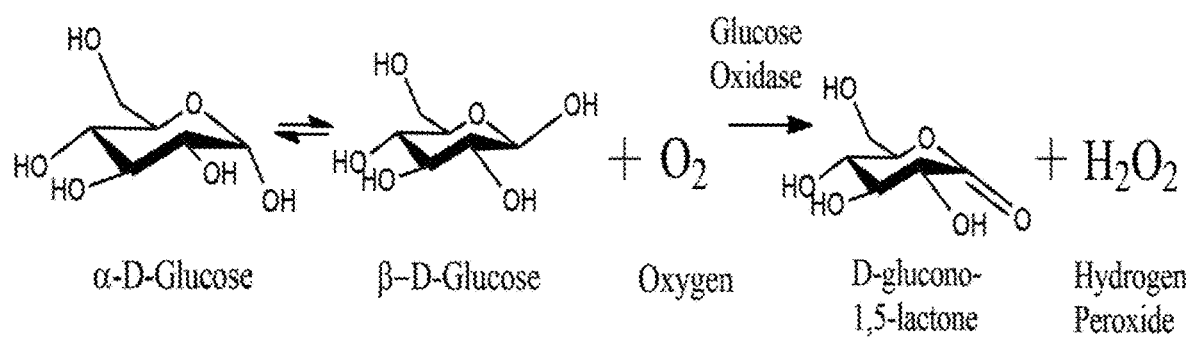
Figure 1C:
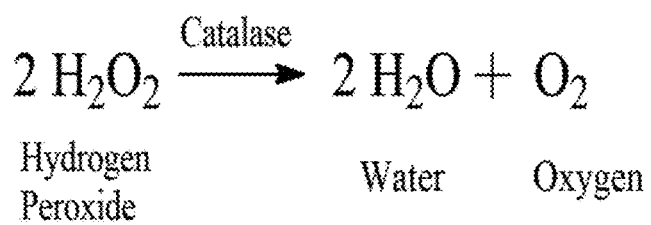

The process of honey production is complicated and involves various proteins secreted by the bees. Although the protein and enzyme composition is variable, three main enzymes take part in the core process of honey production—Invertase, Glucose oxidase (Gox) and Catalase. The concentrations of the enzymes may vary among different honey samples, yet all three enzymes are essential for the creation of honey. Invertase is an enzyme that catalyzes the cleavage of sucrose into fructose and glucose (FIG. 1A). Sucrose is the starting material for honey production and introduction of invertase produces fructose and glucose the two main components of honey. However, honey comprises more fructose than glucose, while invertase produces roughly equal amounts of the two sugars. Glucose oxidase (GOx) catalyzes the oxidation of glucose using molecular oxygen to create hydrogen peroxide and D-glucono-lactone (FIG. 1B). Catalase is an enzyme that decomposes hydrogen peroxide produced by GOx to create water and molecular oxygen (FIG. 1C).

In order to mimic honey production, these three enzymes were chosen for the execution of a synthetic bee-less honey system (Honey Circuit). It was hypothesized that an interplay between these enzymes and the sugars will yield an emulsion with a balanced mix of sugars, that would not be possible to attain in any other way. The incorporation of bacteria for the production of honey can control the enzyme concentration within the emulsion at any given moment in time, and thus allows the introduction of a feed-back mechanism which will facilitate a fine-tuned control of the final sugar ingredients within the emulsion. Thus, making honey using engineered bacteria is akin to manufacturing a biochemical "dimmer" where the concentration of the enzymes that are needed for this process are constantly monitored. The alternative of just mixing enzymes and sugars in an emulsion will not yield the same result, as such a fine-tuned control of enzyme concentration will not be possible. Consequently, given the bacteria's ability to control the production and secretion of the needed enzymes, our system can not only be tuned to produce a honey-like substance, but also a whole family of substances with characterized by varying sugar concentrations, a range of pH levels, viscosities, and peroxide concentrations. Finally, the bacteria can be used to not only fine tune the invertase, glucose oxidase, and catalase enzymes, but also secrete other biomolecules which can further enhance the bacterial honey properties.

The basic design for the system necessitates the fine-tuned expression of invertase, glucose oxidase, and catalase enzymes and secretion of invertase and glucose oxidase into a sucrose emulsion. To do so the bacterial chassis of the gram positive bacteria B. subtilis was selected. B. subtilis is considered a "generally regarded as safe" (GRAS) organism, which like many gram-positive bacteria has the capability of secreting proteins using a signal peptide. To facilitate secretion from the bacteria the gene for each enzyme was encoded downstream of a sequence encoding for a signal peptide (AmyE sequence). A His-tag can optionally be inserted in-frame and downstream of the enzyme. Upon expression, the chimeric signal peptide-enzyme protein will be secreted to the extra-cellular milieu containing sucrose. During secretion the signal peptide is cleaved and the enzyme folds to achieve functionality outside of the cell.

Example 2: Generation of the Honey Circuit

In order to fine-tune the expression of the honey enzymes, controlling the hydrogen peroxide production (a byproduct of the glucose oxidase reaction) is essential for bacterial growth. While B. subtilis can survive in the presence of hydrogen peroxide, to a certain extent, regulating the peroxide producing glucose oxidase (GOx) is important. This regulation can be achieved by controlled expression of the GOx enzyme, by employing a hydrogen peroxide-sensitive promoter. The hydrogen peroxide naturally diffuses into the cells and can then regulate the bacterial promoter. The repressive element in the promoter would be activated by increased hydrogen peroxide levels, which would lead to enzyme expression being inhibited. Thus, in response to hydrogen peroxide GOx protein levels would decrease which would in turn lead to decreased hydrogen peroxide.

Besides regulating hydrogen peroxide levels, the "Honey Circuit" has another important role, which is to maintain a constant sugar composition that simulates the bees' honey content. Without the regulation generated by the circuit, neither the suitable hydrogen peroxide levels nor the correct sugar composition could be obtained. While commercial invertase will reduce the sucrose concentration, producing glucose and fructose, GOx will degrade the glucose until it is all used up. This would ignore the desired fructose to glucose ratio by endlessly decreasing the concentration of glucose and producing a high concentration of hydrogen peroxide, which may eventually kill the bacteria.

Figure 2A:
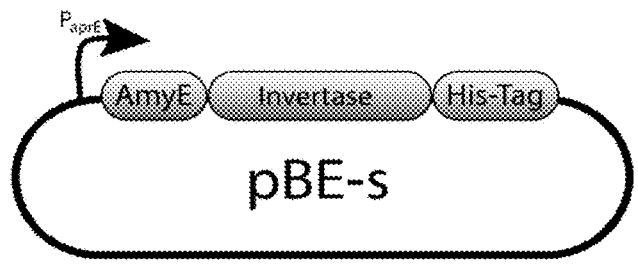
FIGS. 2A-B: Illustration of the plasmids in the Honey Circuit including (2A) a pBE-S containing the signal peptide AmyE and the gene for invertase and (2B) a pBE-S containing the gene for GOx under the control of a repressible promoter.

The honey circuit therefore is composed of two separate modules, that are each encoded on a separate plasmid. The first plasmid (FIG. 2A) contains a signal peptide fused to the invertase gene. As the concentration of sucrose in honey is low, this enzyme does not need to be regulated and it should degrade as much sucrose as possible. The invertase is thus controlled by a constitutively active promoter. The commercial plasmid pBE-S (by TaKaRa) was used as it is designed specifically for the expression of proteins to be secreted from *B. subtilis*.

Figure 2B:
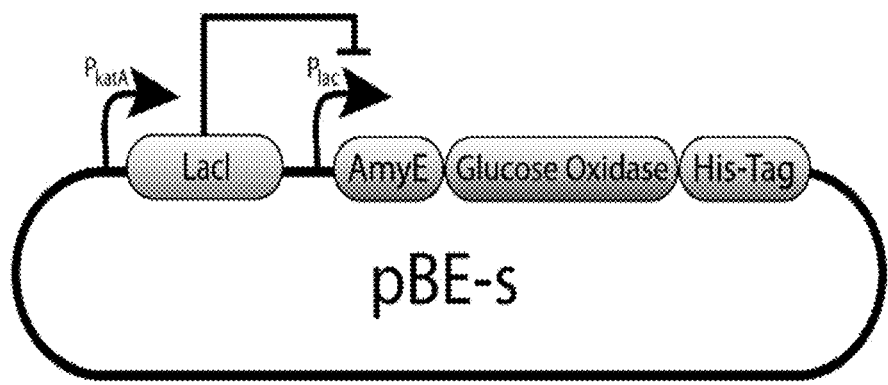

In order to achieve a similar fructose to glucose ratio as found in natural honey, the second plasmid (FIG. 2B) encodes GOx (with a signal peptide and His-tag) under the control of a repressible promoter. The Plac promoter is repressible by the LacI protein and was employed to regulated GOx transcription. LacI was encoded on the same promoter, but under the control of a hydrogen peroxide sensitive promoter. For this purpose, the Pkat promoter was used. This promoter is activated only at increased concentrations of hydrogen peroxide. The result is that at high hydrogen peroxide levels the LacI gene is transcribed and represses GOx transcription. This feedback circuit ensures that when glucose levels fall (which produces high hydrogen peroxide) GOx production is inhibited. This has the two-fold benefit of keeping fructose and glucose in proper balance as well as keeping hydrogen peroxide levels from getting too high. By combining the two plasmids of the invention, the honey circuit mimics the natural process that takes place in the bees' stomach, achieving an auto-regulated synthetic pathway that produces biosynthetic honey.

Example 3: Modeling the Honey Circuit

Figure 3A:
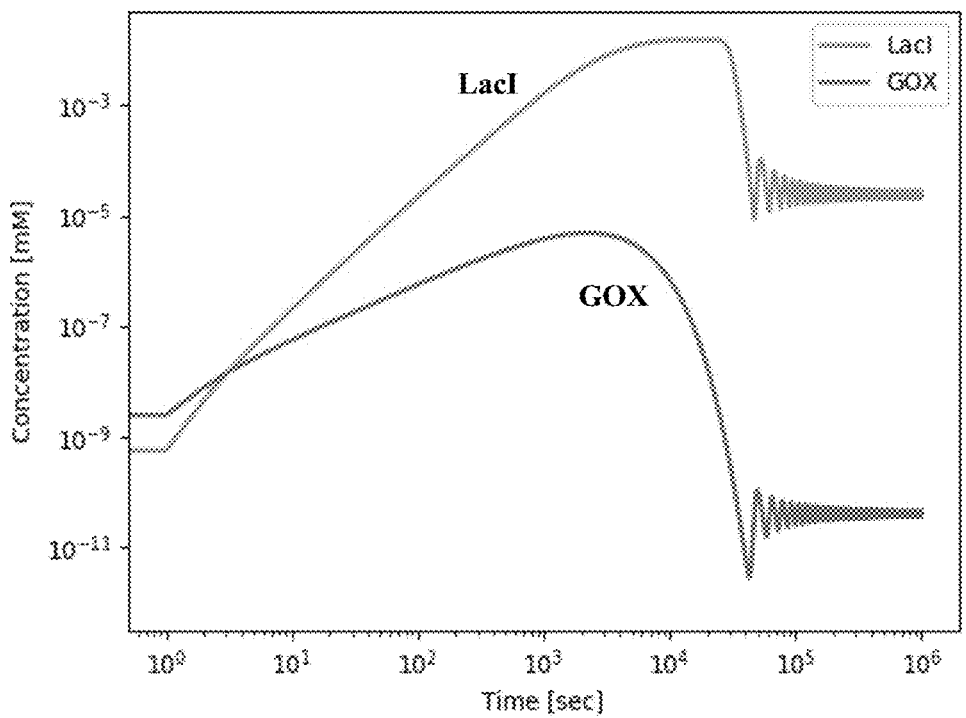
FIGS. 3A-C: Model predictions. (3A) A line graph modeling the stabilization of glucose oxidase secretion in the honey circuit. (3B-C) Line graphs modeling the predicted sugar and peroxide levels in the presence of (3B) a constant level of the enzymes, and (3C) enzymes secreted by the honey circuit system.

To better understand and predict the interplay between the different enzymes, a kinetic model was built which incorporates the dynamic interactions between the enzymes, their secretion from the bacteria, and the influence on pH of the system. First, the model allowed verification that the desired fine-tuned control of enzyme concentration can be achieved with this design. Importantly, the model shows that LacI and therefore GOx both reach an essentially static equilibrium (FIG. 3A). After an initial rise in the concentration of both LacI and Gox, damped oscillations begin to dominate the dynamics, which at later times converge on steady state enzymatic levels. The static balance of LacI and GOx is essential in producing a final composition with the desired glucose levels.

Figure 3B:
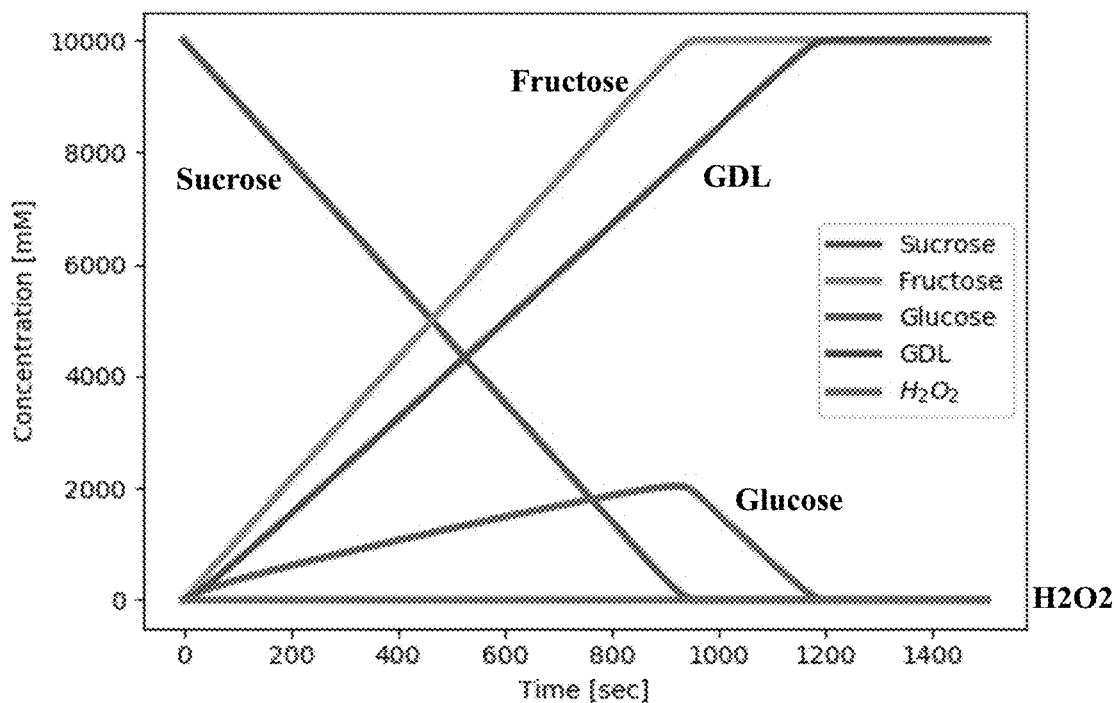
Figure 3C:
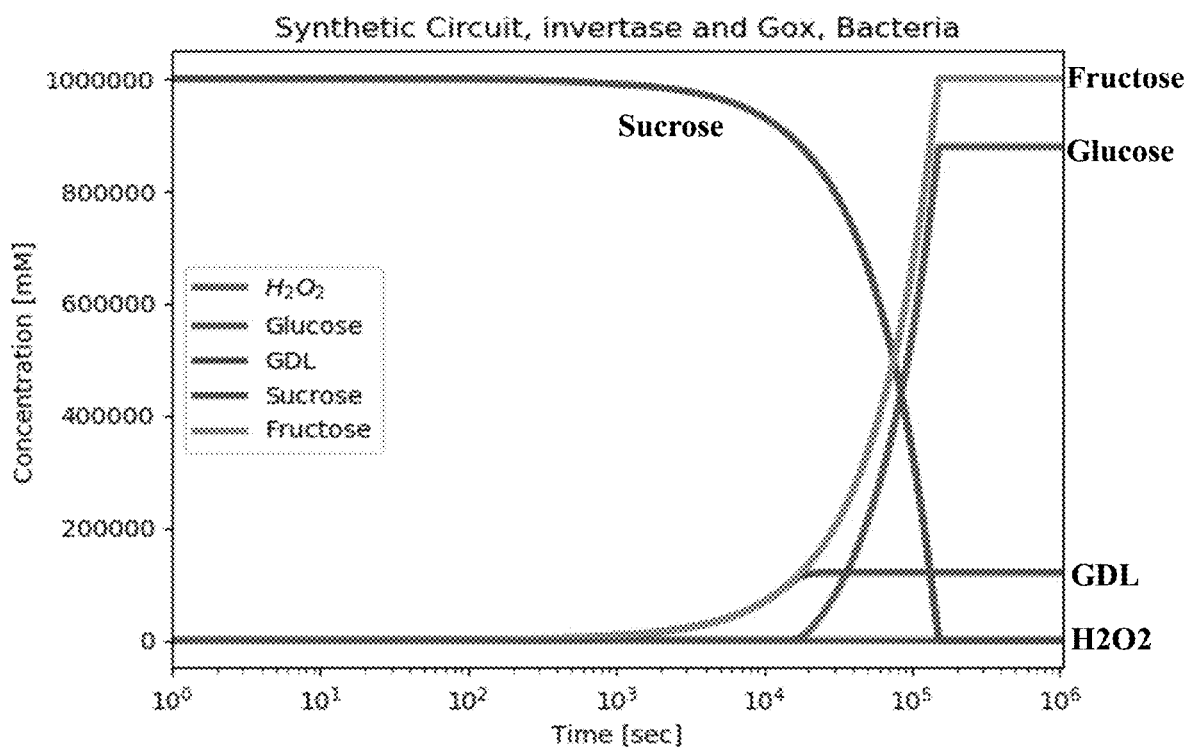

This dynamic is shown in FIGS. 3B and 3C. First the concentrations of the various nonenzymatic components of the system are calculated when purified commercial enzymes are added to a sucrose containing media (FIG. 3B). As would be expected invertase function leads to complete conversion of sucrose to fructose, resulting in the final concentration of fructose being equal to the initial concentration of sucrose. Glucose is also produced by the invertase enzyme, but the GOx enzyme causes rapid conversion of glucose to D-glucono-lactone (DGL). Eventually, every molecule of glucose is converted to DGL and the DGL concentration also reaches the starting concentration of sucrose. Catalase keeps the level of hydrogen peroxide constantly low although a small increase was detected.

The model which includes *B. subtilis* and the honey circuit feedback plasmid shows a markedly different result (FIG. 3C). In the initial stage GOx expression is high and glucose produced is rapidly converted to DGL. However, as hydrogen peroxide levels increase Lac is produced and GOx gets shut off. The half-life of Lac is such that Lac levels remain high enough that GOx remains shut off for the rest of the culture period, and indeed GOx levels rapidly drop below the point at which the enzyme is actively converting glucose to DGL (see FIG. 3A). At this point the invertase is still digesting sucrose and so glucose levels rise in parallel to fructose levels. The result is that final glucose concentrations are significantly closer to the fructose concentrations but are never equal due to the initial conversion of glucose to GDL. As the B. *Subtilis* bacteria naturally expresses catalase, the level of hydrogen peroxide is kept constantly low, although it is above zero. Secretion of catalase is not required as only the intracellular hydrogen peroxide can regulate the responsive promoter.

Example 4: Experimental Verification of Enzyme Function

To verify that the "Honey circuit" works in accordance with the model's predictions, an engineered strain of *B. subtilis* expressing the two plasmids of the circuit was generated. As stated earlier, *B. subtilis* naturally expresses catalase. Various tests were conducted to check the secretion and activity of the main enzymes in the system: invertase, and GOx.

For the expression and secretion tests both bacterial lysate and the supernatant (LB) were tested. First, the samples were concentrated using His-tag column and then SDS-PAGE and Western blot (WB) analyses were employed in order to confirm the presence of the enzymes.

Figure 4A:
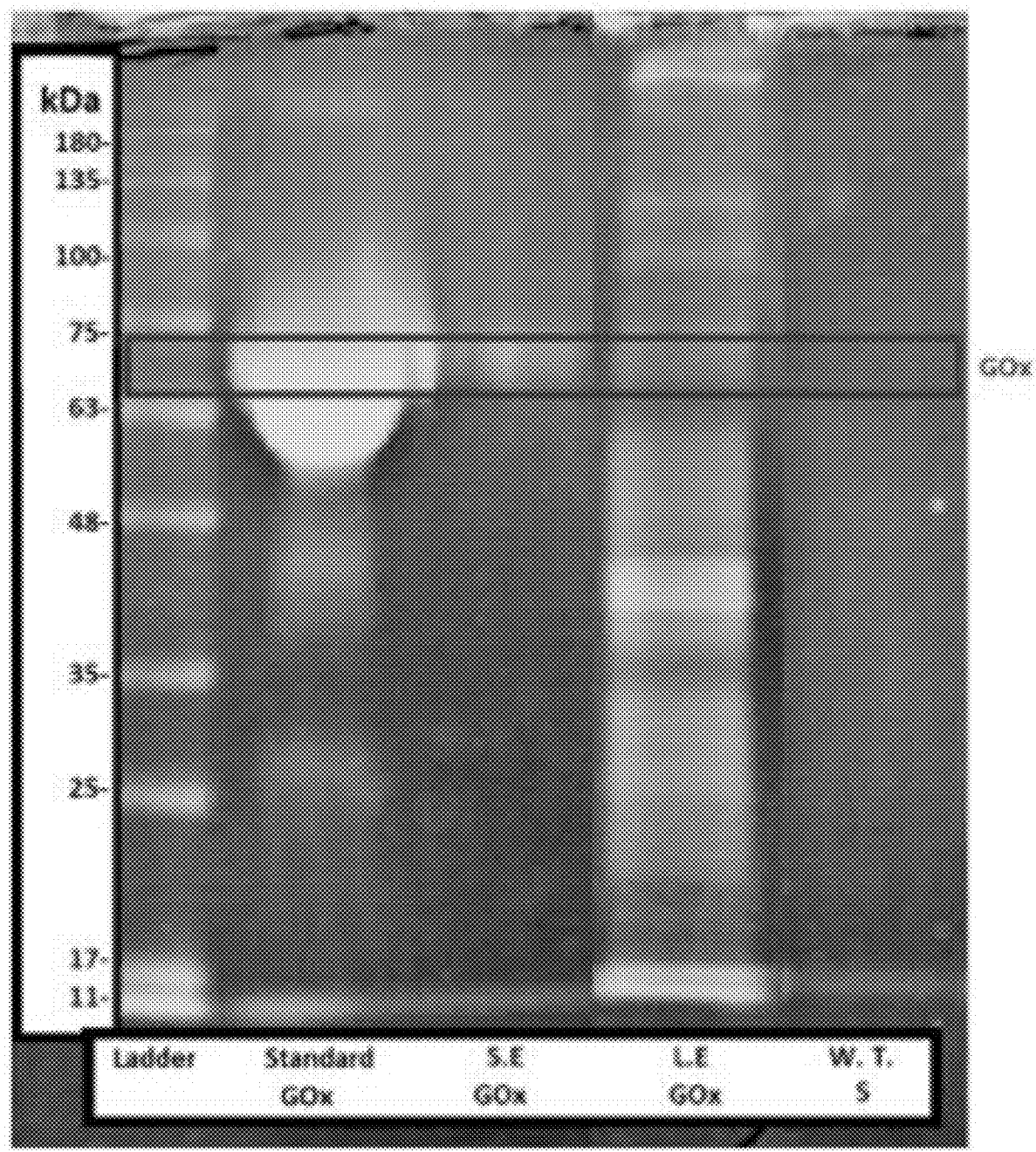
FIGS. 4A-B. Verification of secretion. (4A) Micrograph of SDS-PAGE results for the His-Tag concentrated protein. (4B) Micrograph of a Western Blot with anti-GOx antibodies of the His-Tag concentrated protein.
Figure 4B:
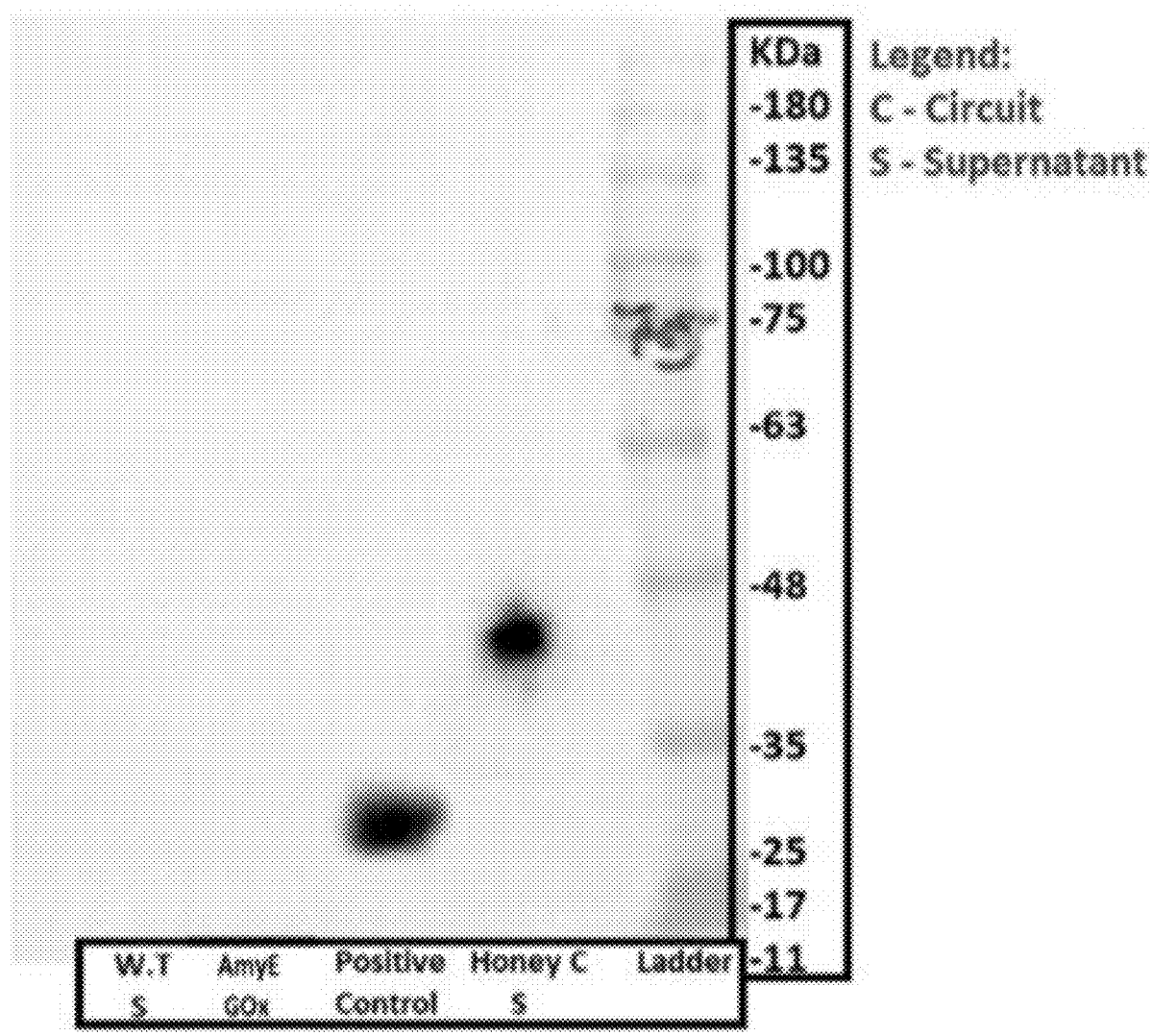

As can be seen in FIG. 4A, there is a weak band corresponding to the size of the standard GOx in both the supernatant and lysate. No band was observed in the WT supernatant sample. A Western Blot (WB) with GOx specific antibodies was also performed (FIG. 4B). The results also showed the presence of the His-tagged enzyme and due to the superior sensitivity, a clear band in the honey circuit supernatant is visible indicating that the engineered bacteria express and secrete the GOx protein.

Figure 5A:
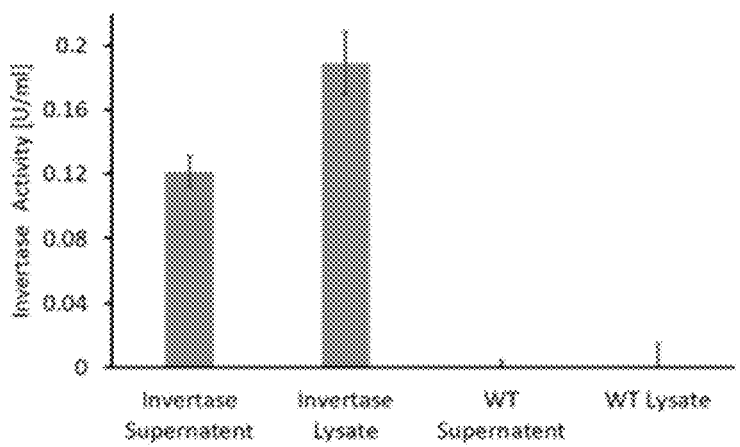
FIGS. 5A-B. Activity Tests. (5A) Bar graph of the activity of invertase in different samples, indicated by the absorbance at 492 nm. (5B) Bar graph of the activity of GOx and in different samples, indicated by the absorbance at 416 nm.
Figure 5B:
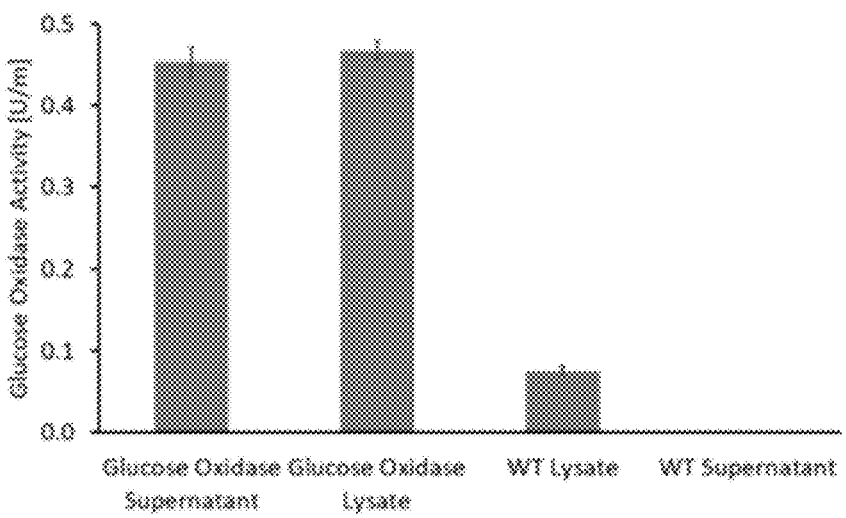

In FIG. 5A results of an invertase enzyme activity test (reducing sugar test) for both the supernatant and lysate of the honey circuit are presented. As can be seen the invertase is fully functional and is successfully secreted into the supernatant. No invertase activity is observed in wild-type *B. subtilis*. In FIG. 5B results of a GOx enzyme activity test (presence of hydrogen peroxide) for both the supernatant and lysate of the honey circuit are presented. The results confirm that both the GOx is fully functional and is successfully secreted into the extra-cellular milieu.

Example 5: Experimental Verification of Circuit Function

Next the behavior of the whole genetic circuit was tested in the presence of glucose or under different concentrations of hydrogen peroxide, in order to determine whether the glucose oxidase (GOx) production is being regulated properly and reaches a steady state.

Figure 6:
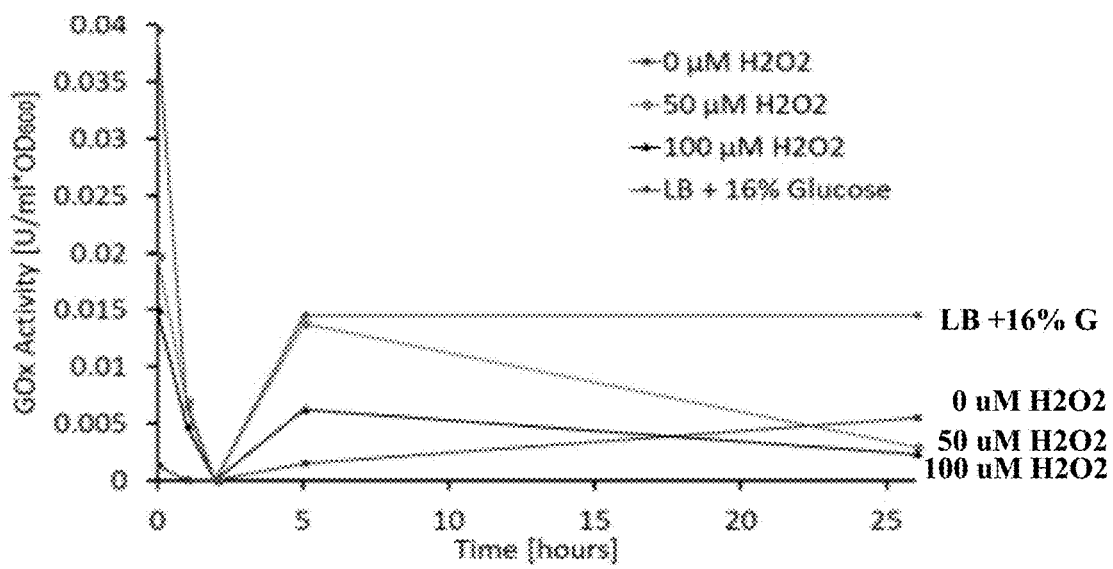
FIG. 6. A line graph showing GOx activity in the supernatant from *B. subtilis* cells grown in various conditions.

Given the model's predictions for damped oscillations, it was hypothesized that GOx enzyme expression will exhibit dynamics that will be reminiscent of at least one oscillatory cycle prior to reaching steady state. After reaching steady state, the levels of GOx, hydrogen peroxide, and LacI should remain balanced. The *B. subtilis* cells were cultured in LB media supplemented with 16% glucose and GOx activity in the supernatant was measured at various time points. The results are plotted in FIG. 6, and indeed provide evidence for one oscillatory cycle occurring with the first 5 hours for all peroxide concentrations tested followed by subsequent convergence on various levels of steady state GOx function.

The *B. subtilis* is grown in a solution containing 20-50% sucrose and the concentration of fructose and glucose present in the media is monitored over time. The accuracy of the model is compared to the actual concentrations present in the solution. After degradation of sucrose is complete the relative final concentrations of fructose and glucose in the bee-less honey are compared to bee-produced honey.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A kit comprising:
   i. a first expression vector polynucleotide comprising at least one first promoter operatively linked to a first open reading frame, wherein said first open reading frame encodes a signal peptide and an invertase enzyme, wherein said invertase enzyme is encoded by a sequence comprising SEQ ID NO: 4 or SEQ ID NO: 5 or a sequence homologous thereto that converts one molecule of sucrose into one molecule of glucose and one molecule of fructose; and
   ii. a second expression vector polynucleotide comprising a repressible promoter operatively linked to a second open reading frame, wherein said second open reading frame encodes a signal peptide and a glucose oxidase enzyme, wherein said glucose oxidase enzyme is encoded by a sequence comprising SEQ ID NO: 6 or 7 or a sequence homologous thereto that converts one glucose molecule into one molecule of glucono-1,5-lactone and one molecule of hydrogen peroxide, and wherein said repressible regulatory element inhibits transcription of said second open reading frame in response to hydrogen peroxide.

2. The system kit of claim 1, wherein
   wherein said signal peptide is operatively linked to said enzyme to induce secretion of said enzyme by a cell.

3. The kit of claim 1, wherein said promoter is a bacterial promoter, said first promoter is a constitutive promoter or both.

4. The kit of claim 1, wherein said repressible promoter inhibits transcription of said second open reading frame and said inhibition is proportional to hydrogen peroxide levels.

5. The kit of claim 4, further comprising a hydrogen peroxide sensitive promoter operatively linked to a third reading frame, wherein said third reading frame encodes a repressor of said repressible promoter and wherein said hydrogen peroxide sensitive promoter induces transcription of said third reading frame in response to hydrogen peroxide.

6. The kit of claim 5, wherein said hydrogen peroxide sensitive regulatory element is a Pkat promoter, said repressor is LacI, said repressible regulatory element is a Plac promoter, or a combination thereof.

7. The kit of claim 5, further comprising a fourth polynucleotide molecule comprising a regulatory element operatively linked to a fourth open reading frame, wherein said fourth open reading frame encodes a catalase enzyme and wherein said catalase is functional to convert hydrogen peroxide to water and oxygen.

8. A cell comprising the first expression vector polynucleotide and second expression vector polynucleotide of the kit of claim 1.

9. The cell of claim 8, wherein said cell is a bacterial cell, is a B. subtilis cell, comprises endogenous expression of a catalase enzyme, or a combination thereof.

10. The cell of claim 8, wherein said polynucleotides are expression vectors functional within said cell, said signal peptides are functional within said cells to induce secretion of proteins to which said signal peptides are operatively linked or both.

11. A composition comprising the cell of claim 8 cultured in a solution comprising sucrose.

12. The composition of claim 11, wherein said solution comprises between 20-50% sucrose.

13. The composition of claim 11, wherein said cell and growth media for said cell devoid of sucrose are within a semipermeable container and said semipermeable container is within said solution comprising sucrose and wherein said semipermeable container is configured to allow invertase and glucose oxidase to diffuse out of said growth media into said solution comprising sucrose and not allow glucose to diffuse from said media comprising glucose into said growth media.

14. A composition comprising the cell of claim 8 and growth media for said cell devoid of sucrose within a semipermeable container, wherein said semipermeable container is configured to allow invertase and glucose oxidase to diffuse out of said growth media and not allow glucose to diffuse into said growth media.

15. A method for producing bee-less honey, the method comprising culturing the cell of claim 8 in a solution comprising sucrose, thereby producing bee-less honey.

16. The method of claim 15, wherein
 a. said solution comprising sucrose comprises between 20-50% sucrose;
 b. said culturing comprises culturing the composition of claim 15 within said solution comprising sucrose;
 c. said culturing further comprising adding sucrose to said solution if sucrose concentration in said solution is below a predetermined threshold; or
 d. a combination thereof.

17. An artificial honey solution produced by a method of claim 15.

18. An artificial honey solution, comprising at least 40% fructose, at least 30% glucose, at most 10% sucrose and at most 20% water.

19. The kit of claim 1, being for use in transfecting or infecting a bacterial cell.

20. The kit of claim 1, wherein said invertase is encoded by a sequence comprising SEQ ID NO: 4 or SEQ ID NO: 5 and said glucose oxidase is encoded by a sequence comprising SEQ ID NO: 6 or SEQ ID NO: 7.

* * * * *

SEQUENCE LISTING

```
<160> NUMBER OF SEQ ID NOS: 13

<210> SEQ ID NO 1
<211> LENGTH: 66
<212> TYPE: DNA
<213> ORGANISM: Bacillus subtilis

<400> SEQUENCE: 1
ataactattt tataataatt ataaaataat attgactttt tacttagaga tgatattatg      60
ttctta                                                                 66

<210> SEQ ID NO 2
<211> LENGTH: 101
<212> TYPE: DNA
<213> ORGANISM: Escherichia coli

<400> SEQUENCE: 2
ctcgagggta aatgtgagca ctcacaattc attttgcaaa agttgttgac tttatctaca      60
aggtgtggca taatgtgtgt aattgtgagc ggataacaat t                         101

<210> SEQ ID NO 3
<211> LENGTH: 1086
<212> TYPE: DNA
<213> ORGANISM: Escherichia coli

<400> SEQUENCE: 3
atgaaaccag taacgttata cgatgtcgca gagtatgccg gtgtctctta tcagaccgtt      60
tcccgcgtgg tgaaccaggc cagccacgtt tctgcgaaaa cgcgggaaaa agtggaagcg     120
gcgatggcgg agctgaatta cattcccaac cgcgtggcac aacaactggc gggcaaacag     180
tcgttgctga ttggcgttgc cacctccagt ctggccctgc acgcgccgtc gcaaattgtc     240
gcggcgatta aatctcgcgc cgatcaactg ggtgccagcg tggtggtgtc gatggtagaa     300
cgaagcggcg tcgaagcctg taaaacggcg gtgcacaatc ttctcgcgca acgcgtcagt     360
gggctgatca ttaactatcc gctggatgac caggatgcca ttgctgtgga agctgcctgc     420
actaatgttc cggcgttatt tcttgatgtc tctgaccaga cacccatcaa cagtattatt     480
ttctcccatg aagacggtac gcgactgggc gtggagcatc tggtcgcatt gggtcaccag     540
caaatcgcgc tgttagcggg cccattaagt tctgtctcgg cgcgtctgcg tctggctggc     600
```

-continued

| | |
|---|---|
| tggcataaat atctcactcg caatcaaatt cagccgatag cggaacggga aggcgactgg | 660 |
| agtgccatgt ccggttttca acaaaccatg caaatgctga atgagggcat cgttcccact | 720 |
| gcgatgctgg ttgccaacga tcagatggcg ctgggcgcaa tgcgcgccat taccgagtcc | 780 |
| gggctgcgcg ttggtgcgga tatctcggta gtgggatacg acgataccga agacagctca | 840 |
| tgttatatcc cgccgtcaac caccatcaaa caggattttc gcctgctggg caaaccagc | 900 |
| gtggaccgct tgctgcaact ctctcagggc caggcggtga agggcaatca gctgttgccc | 960 |
| gtctcactgg tgaaaagaaa aaccacccctg cgcccaata cgcaaaccgc ctctccccgc | 1020 |
| gcgttggccg attcattaat gcagctggca cgacaggttt cccgactgga aagcgggcag | 1080 |
| taataa | 1086 |

<210> SEQ ID NO 4
<211> LENGTH: 1767
<212> TYPE: DNA
<213> ORGANISM: Aspergillus niger

<400> SEQUENCE: 4

| | |
|---|---|
| atgaagcttc aaacggcttc cgtactgctc ggcagtgctg cggctgcctc tccttcaatg | 60 |
| cagacgcggg cctccgtgat catcgactac aatgtcgctc ctccaaacct ctccaccctg | 120 |
| cccaatggct ccctcttcga acatggcgt ccccgcgccc acgtcctgcc cccaaacggc | 180 |
| agatcggtga cccctgcctg cattacaccg atcccgccac gggcctcttt ccacgtcggc | 240 |
| ttccttcacg atggcagcgg catctccagt gccaccaccg atgacctacc cacctaccaa | 300 |
| gacctcaacc aaggcaacca agtcattgtc cccggaggca tcaacgaccc cgtcgctgtc | 360 |
| ttcgacggct cagtcatccc caacggcatc aacggcctcc ccaccctcct ctacacctcc | 420 |
| gtctcctacc tccccatcca ctggtccatc ccctacaccc gcggcagtga acccaatcc | 480 |
| ctcgccgtct cctccgacgg cggcagcaac ttcaccaagc tcgaccaggg ccccgtcatc | 540 |
| cctggccctc ccttcgccta acgtcacc gcattccggg accctacgt cttccaaaac | 600 |
| cccacactcg aatccctcct ccacagcaag aacaacacct ggtacaccgt catctccggt | 660 |
| ggtctgcacg aaaagggccc cgcccaattc ctctaccgtc agtacgactc ggacttccag | 720 |
| tactgggagt acctcggcca atggtggcac gaacccacca actccacctg gggtaacggc | 780 |
| acctgggccg gccgctgggc cttcaacttc gagaccggca acgtcttcag tctcgacgag | 840 |
| tacggataca ccccacggg ccagatcttc accaccatcg gcaccgaggg ctctgacctg | 900 |
| cccgtcgtgc cccagctcac cagcatccac gacatgctct gggtgtccgg tacagtctcc | 960 |
| cgcaatggct ctgtctcttt caccccaac atggcgggct cctcgattg gggcttctcc | 1020 |
| tcttacgctg ctgccggaaa ggttctcccc tcgacttctc tgccttccac gaagagcggc | 1080 |
| gccccggaac gcttcatctc gtacgtctgg ctgtccggtg acctgttcga acaggccgaa | 1140 |
| ggattcccca cgaaccagca gaattggacc ggtacgctgc tgcttccgcg tgagttgcgc | 1200 |
| gtgctgtata tccccaatgt ggtggacaat gctctggccc gggagtctgg tgcctcgtgg | 1260 |
| caggtcgtga gcagcgacag cagtgcgggc accgtcgagc tgcagacgct gggtatctcc | 1320 |
| attgcccggg aaaccaaggc cgcgttgctg tcgggaacgt cgttcactga gtccggccgc | 1380 |
| accctgaaca gcagcggtgt tgttccgttc aagcgctcgc catccgagaa gttcttcgtt | 1440 |
| ctgtccgcac agctgtcctt ccctgcgtcg gctagaggat cgggacttaa gagtggattc | 1500 |
| cagatcctct catcggagca cgaaagtacc accgtgtact accaattctc gaatgagtcg | 1560 |

| | |
|---|---|
| attatcgtcg atcgcagcaa cactagtgct gcggcgcgca cgactgatgg catcgatagc | 1620 |
| agtgcagaag ctggcaagtt gcgtctattt gacgtgctga atggcggaga gcaggccatt | 1680 |
| gagacgctag atttgactct cgtggtggat aactccgtgt tggagatgta tgccaatggt | 1740 |
| cggtttgcgt tgagtacttg ggttcgg | 1767 |

<210> SEQ ID NO 5
<211> LENGTH: 1767
<212> TYPE: DNA
<213> ORGANISM: Artificial
<220> FEATURE:
<223> OTHER INFORMATION: Synthetic

<400> SEQUENCE: 5

| | |
|---|---|
| atgaagcttc aaacggcttc agtactgctc ggcagcgctg cggctgcctc tccttcaatg | 60 |
| cagacgcggg cctcagtgat catcgactac aatgtcgctc ctccaaacct ctcaaccctg | 120 |
| ccgaatggct cactcttcga acatggcgt ccgcgcgccc acgtcctgcc gccaaacggc | 180 |
| agatcagtga cccctgcctg cattacaccg atcccgccac gggcctcttt ccacgtcggc | 240 |
| ttccttcacg atggcagcgg catctcaagc gccaccaccg atgacctgcc gacctaccaa | 300 |
| gacctcaacc aaggcaacca agtcattgtc ccgggaggca tcaacgaccc ggtcgctgtc | 360 |
| ttcgacggct cagtcatccc gaacggcatc aacggcctcc cgaccctcct ctacacctca | 420 |
| gtctcatacc tcccgatcca ctggtcaatc ccgtacaccc gcggcagcga gacccaatca | 480 |
| ctcgccgtct catcagacgg cggcagcaac ttcaccaagc tcgaccaggg cccggtcatc | 540 |
| cctggccctc cgttcgccta caacgtcacc gcattccggg accgtacgt cttccaaaac | 600 |
| ccgacactcg aatcactcct ccacagcaag aacaacacct ggtacaccgt catctcaggt | 660 |
| ggtctgcacg aaaagggccc ggcccaattc ctctaccgtc agtacgactc agacttccag | 720 |
| tactgggagt acctcggcca atggtggcac gaaccgacca actcaacctg ggtaacggc | 780 |
| acctgggccg gacgctgggc cttcaacttc gagaccggca cgtcttcag cctcgacgag | 840 |
| tacggataca cccgcacgg ccagatcttc accaccatcg gcaccgaggg ctctgacctg | 900 |
| ccggtcgtgc cgcagctcac cagcatccac gacatgctct gggtgtcagg tacagtctca | 960 |
| cgcaatggct ctgtctcttt caccccgaac atggcgggct tcctcgattg gggcttctca | 1020 |
| tcttacgctg ctgccggaaa ggttctcccg tcaacttctc tgccttcaac gaagagcggc | 1080 |
| gccccggaac gcttcatctc atacgtctgg ctgtcaggtg acctgttcga acaggccgaa | 1140 |
| ggattcccga cgaaccagca gaattggacc ggtacgctgc tgcttccgcg tgagttgcgc | 1200 |
| gtgctgtata tcccgaatgt ggtggacaat gctctggccc gggagtctgg tgcctcatgg | 1260 |
| caggtcgtga gcagcgacag cagcgcgggc accgtcgagc ttcagacgct gggtatctca | 1320 |
| attgcccggg aaaccaaggc cgcgttgctg tcaggaacgt cattcactga gtcaggacgc | 1380 |
| accctgaaca gcagcggtgt tgttccgttc aagcgctcac catcagagaa gttcttcgtt | 1440 |
| ctgtcagcac agctgtcatt ccctgcgtca gctagaggat caggacttaa gagcggattc | 1500 |
| cagatcctct catcagagca cgaaagcacc accgtgtact accaattctc aaatgagtca | 1560 |
| attatcgtcg atcgcagcaa cactagcgct gcggcgcgca cgactgatgg catcgatagc | 1620 |
| agcgcagaag ctggcaagtt gcgtctgttt gacgtgctga atggcggaga gcaggccatt | 1680 |
| gagacgctgg atttgactct cgtggtggat aactcagtgt tggagatgta tgccaatggt | 1740 |
| cggtttgcgt tgagcacttg ggttcgg | 1767 |

```
<210> SEQ ID NO 6
<211> LENGTH: 1815
<212> TYPE: DNA
<213> ORGANISM: Aspergillus niger

<400> SEQUENCE: 6
atgcagactc tccttgtgag ctcgcttgtg gtctccctcg ctgcggccct cccacactac      60
atcaggagca atggcatcga agccagcctc ctgactgacc ccaaggaggt tgccggccgc     120
actgtcgact acatcatcgc tggtggaggt ctgactggac tcaccactgc tgcccgtctg     180
acggagaacc ccgatatcac tgtgcttgtc atcgaaagtg gctcctacga gtctgacaga     240
ggtcctatca ttgaggacct gaacgcttac ggtgacattt ttggcagcag tgtggaccac     300
gcctacgaga ctgtcgagct cgccaccaac aatcagactg cgctgatccg ctccggaaat     360
ggtctcggtg gctctaccct cgtcaacggt ggcacctgga ctcgccccca caaggcacaa     420
gttgactcat gggagaccgt cttcggaaat gagggctgga actgggacag cgtggccgcc     480 tactcccctcc aggctgagcg tgctcgcgca ccaaatgcca aacagattgc tgctggccac     540
tactttaatg catcctgcca tggtatcaat ggtactgtcc acgccggacc ccgcgatacc     600
ggtgatgact actcccccat cgtcaaggct ctcatgagcg ctgtcgaaga caggggcgtt     660
cccaccaaga aggacttggg atgcggtgac ccccatggtg tgtccatgtt ccccaacacc     720
ttgcacgaag accaagtgcg ctctgatgcc gctcgcgaat ggctcctccc caactaccag     780
cgtcccaacc tgcaagtcct cactggacag tatgttggaa aggtcctgct cagccagaac     840
gctaccacac tcgtgccgt tggcgtgaa ttcggcaccc acaagggcaa cacccacaac     900
gtctacgcta agcacgaggt cctcctggcc gctggatccg ctgtctctcc caccatcctc     960
gaatattccg gtatcggaat gaagtccatt ctagagcctc ttggaattga caccgtcgtt    1020
gacctgcccg ttggtctcaa ccttcaggac cagaccacct ctaccgtccg ctcacgcatt    1080
acctccgccg gtgccggaca gggacaggcc gcttggttcg ctaccttcaa cgagaccttt    1140
ggcgactacg ccgaaaaggc tcacgagctg ctcaacacca gctggagca gtgggccgaa    1200 gaggccgtcg cccgtggcgg attccacaac accaccgctt tgctcatcca gtacgagaac    1260
taccgcgact ggatcgtcaa ggacaatgtc gcatactcgg aactcttcct cgacacggcc    1320
ggagtggcca gtttcgatgt gtgggatctt ctgcccttca ctagaggata cgtacacatc    1380
ctcgacaagg accctacct ccgccatttc gcatacgacc ctcagtactt tctcaacgag    1440
cttgacctgc tcggccaggc tgccgccact cagctggccc gcaacatctc caactccggt    1500
gccatgcaaa cttatttcgc tggagagact attcccggtg acaacctcgc gtatgatgcc    1560
gacttgagcg cctgggttga gtatatcccg tacaacttcc gccctaacta ccatggtgtg    1620
ggtacttgct ccatgatgcc gaaggagatg ggcggtgttg tcgacaatgc tgcccgtgtg    1680
tatggtgtgc agggactgcg agtcatcgat ggttctattc cccctacgca aatgtcgtcc    1740
catgttatga cggtcttta tgccatggcc ttgaagattg cggatgccat cttggcggat    1800
tatgcttcca tgcag                                                       1815

<210> SEQ ID NO 7
<211> LENGTH: 1815
<212> TYPE: DNA
<213> ORGANISM: Artificial
<220> FEATURE:
<223> OTHER INFORMATION: Synthetic

<400> SEQUENCE: 7
```

-continued

```
atgcagactc tccttgttag ctcacttgtg gtctccctcg ctgcggccct gccacactac    60
atcagaagca atggcattga agccagcctc ctgactgatc cgaaggatgt ctccggacgc   120
acggtcgact acatcatcgc tggtggaggt ctgactggac tcaccaccgc tgctcgtctg   180
acggagaacc cgaacatcag tgtgctcgtc atcgaaagtg ctcctacga gtcagacaga   240
ggtcctatca ttgaggacct gaacgcctac ggcgacatct ttggcagcag tgtagaccac   300
gcctacgaga ccgtggagct ggctaccaac aatcaaaccg cgctgatccg ctccggaaat   360
ggtctcggtg ctctactct ggtgaatggt ggcacctgga ctcgcccgca aaggcacag     420
gttgactctt gggagactgt ctttggaaat gagggctgga actgggacaa tgtggccgcc   480
tactccctcc aggctgagcg tgctcgcgca ccaaatgcca acagatcgc tgctggccac    540
tacttcaacg catcctgcca tggtgttaat ggtactgtcc atgccggacc gcgcgacacc   600
ggcgatgact attctccgat cgtcaaggct ctcatgagcg ctgtcgaaga ccggggcgtt   660
ccgaccaaga aagacttcgg atgcggtgac ccgcatggtg tgtccatgtt cccgaacacc   720
ttgcacgaag accaagtgcg ctccgatgcc gctcgcgaat ggctgcttcc gaactaccaa   780
cgtccgaacc tgcaagtcct gaccggacag tatgttggta aggtgctcct tagccagaac   840
ggcaccaccc cgcgtgccgt tggcgtggaa tttggcaccc acaagggcaa cacccacaac   900
gtttacgcta agcacgaggt cctcctggcc gcgggctccg ctgtctctcc gacaatcctc   960
gaatattccg gtatcggaat gaagtccatc ctggagccgc ttggtatcga caccgtcgtt  1020
gacctgccgg tcggcttgaa cctgcaagac cagaccaccg ctaccgtccg ctcccgcatc  1080
acctctgctg gtgcaggaca gggacaggcc gcttggttcg ccaccttcaa cgagaccttt  1140
ggtgactatt ccgaaaaggc acacgagctg ctcaacacca agctggagca gtgggccgaa  1200
gaggccgtcg cccgtggcgg attccacaac accaccgcct gctcatcca gtacgagaac   1260
taccgcgact ggattgtcaa ccacaacgtc gcgtactcag aactcttcct cgacactgcc  1320
ggagtagcca gcttcgatgt gtgggacctt ctgccgttca cccgtggata cgttcacatc  1380
ctcgacaagg acccgtacct tcaccacttc gcctacgacc ctcagtactt cctcaacgag  1440
ctggacctgc tcggtcaggc tgccgctact caactggccc gcaacatctc caactccggt  1500
gccatgcaga cctacttcgc tggggagact atcccgggtg ataacctcgc gtatgatgcc  1560
gatttgagcg cctggactga gtacatcccg taccacttcc gtcctaacta ccatggcgtg  1620
ggtacttgct ccatgatgcc gaaggagatg ggcggtgttg ttgataatgc tgcccgtgtg  1680
tatggtgtgc agggactgcg tgtcattgat ggttctattc ctcctacgca aatgtcatcc  1740
catgtcatga cggtgttcta tgccatggcg ctgaaaattt cagatgctat cttggaagat  1800
tatgcttcca tgcag                                                   1815
```

<210> SEQ ID NO 8
<211> LENGTH: 27
<212> TYPE: PRT
<213> ORGANISM: Bacillus subtilis

<400> SEQUENCE: 8

Met Phe Ala Lys Arg Phe Lys Thr Ser Leu Leu Pro Leu Phe Ala Gly
1               5                   10                  15
Phe Leu Leu Leu Phe His Leu Val Leu Ala Gly
            20                  25

<210> SEQ ID NO 9
<211> LENGTH: 33

```
<212> TYPE: PRT
<213> ORGANISM: Bacillus subtilis

<400> SEQUENCE: 9

Met Phe Ala Lys Arg Phe Lys Thr Ser Leu Leu Pro Leu Phe Ala Gly
1               5                   10                  15

Phe Leu Leu Leu Phe His Leu Val Leu Ala Gly Pro Ala Ala Ala Ser
            20                  25                  30

Ala

<210> SEQ ID NO 10
<211> LENGTH: 81
<212> TYPE: DNA
<213> ORGANISM: Bacillus subtilis

<400> SEQUENCE: 10
atgtttgcaa acgattcaa aacctcttta ctgccgttat tcgctggatt tttattgctg     60
tttcatttgg ttctggcagg a                                              81

<210> SEQ ID NO 11
<211> LENGTH: 99
<212> TYPE: DNA
<213> ORGANISM: Bacillus subtilis

<400> SEQUENCE: 11
atgtttgcaa acgattcaa aacctcttta ctgccgttat tcgctggatt tttattgctg     60
tttcatttgg ttctggcagg accggcggct gcgagtgct                           99

<210> SEQ ID NO 12
<211> LENGTH: 9
<212> TYPE: PRT
<213> ORGANISM: Bacillus subtilis

<400> SEQUENCE: 12

Arg Pro Val His Ile Trp Ser Ser Val
1               5

<210> SEQ ID NO 13
<211> LENGTH: 27
<212> TYPE: DNA
<213> ORGANISM: Bacillus subtilis

<400> SEQUENCE: 13
cggccggtgc acatatggag ctcggta                                        27
```